(12) United States Patent
Phillips et al.

(10) Patent No.: US 6,210,913 B1
(45) Date of Patent: *Apr. 3, 2001

(54) MODULATION OF INTEGRIN-MEDIATED SIGNAL TRANSDUCTION

(75) Inventors: David R. Phillips, San Mateo; Deborah Ann Law, San Francisco; Lisa Nannizzi Alaimo, Los Altos, all of CA (US)

(73) Assignee: COR Therapeutics, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,607

(22) Filed: Oct. 18, 1996

Related U.S. Application Data

(60) Provisional application No. 60/005,567, filed on Oct. 18, 1995.

(51) Int. Cl.[7] .................... G01N 33/53; G01N 33/567; G01N 33/555; A61K 38/00

(52) U.S. Cl. .................... 435/7.8; 435/7.2; 435/7.21; 435/7.24; 436/501; 436/503; 530/324; 530/325

(58) Field of Search .................... 435/7.2, 7.8, 7.21, 435/7.24; 436/501, 503; 530/324, 325

(56) References Cited

U.S. PATENT DOCUMENTS

| | | |
|---|---|---|
| 5,192,746 | 3/1993 | Lobl et al. . |
| 5,260,277 | 11/1993 | McKenzie . |
| 5,580,979 | 12/1996 | Bachovchin . |

OTHER PUBLICATIONS

Mikayama, T et al. Molecular Cloning and Functional Expression of a CDNA Encoding Glycocylation Inhibiting Factor P.N.A.S (90) 10056–10060 Nov. 1993.*
Scarborough et al. J. Biol. Chem. 268:1066–1073 (1993).*
Fox et al. J. Biol. Chem. 268:25973–25964 (1993).*
Dorahy et al. Biochem. J. 309: 481–490 (1995).*
Argraves, W. S. et al., *Cell* 58:623–629 (1989).
Bartfeld, N. S. et al., *J Biol Chem* 268:17270–17276 (1993).
Chen, Y. P. et al., *J. Cell Biol* 269:18307–18310 (1994).
Chen, Y.–P. et al., *Proc Natl Acaid Sci USA* 89:10169–10173 (1992).
Clark et al., *Science* 268:233–239 (1995).
Elmore, M. A. et al., *FEBS* 269:283–287 (1990).
Filardo, E. J. et al., *J Cell Biol* 130:441–450 (1995).
Findik, D. et al., *FEBS* 262:1–4 (1990).
Fitzgerald, L. et al., *J Biol Chem* 262–3936–3939 (1987).
Ginsberg, M. H. et al., *Curr Opin Cell Biol* 4:766–771 (1992).
Ginsberg, M. H. et al., *Thromb Haemostasis* 70:87–93 (1993).
Ginsberg, M. H. et al., *Stem Cells*, 13:38–46 (1995).
Grinblat, Y. et al., *Development* 120:91–102 (1994).
Hannigan, G. E. et al., *Nature* 379:91–96 (1996).
Hayashi, Y. et al., *J Cell Biol* 110:175–184 (1990).
Hibbs, M. L. et al., *J Exp Med* 174:1227–1238 (1991).
Hillary, C. A. et al., *J Biol Chem* 266:14663–14669 (1991).
Hirst, R. et al., *PNAS USA* 83:6470–6474 (1986).
Horwitz, A., et al., *Nature* 320:531–533 (1986).
Huang, M–M. et al., *J Cell Biol* 122:473–483 (1993).
Hughes, P. E. et al., *J Biol Chem* 270:12411–12417 (1995).
Hynes, R. O., *Cell* 69:11–25 (1992).
Johansson, M.W. et al., *J Cell Biol* 126:1299–1309 (1994).
Juliano, R. L. et al., *Cell Biol* 120:577–585 (1993).
Kieffer, N. et al., *J Cell Biol* 113:451–461 (1991).
LaFlamme, S. E. et al., *J Cell Biol* 126:1287–1298 (1994).
Lanza, F. et al.,*J Biol Chem* 266:10638–10645 (1991).
Luscinskas et al., *FASEB J* 8:929–938 (1994).
O'Toole, T. E. et al., *Cell Regul* 1:883–893 (1990).
O'Toole, T. E. *J Biol Chem* 270:8553–8558 (1995).
Otey, C. A. et al., *J Biol Chem* 268:21193–21197 (1993).
Parise, L. V. et al., *Blood* 75:2363–2368 (1990).
Phillips D. R. et al., *Blood* 71:831–843 (1988).
Phillips, D. R. et al., *cell* 65:359–362 (1991).
Reszka, A. A. *J Cell Biol* 117:1321–1330 (1992).
Rouslahti, E., *J Clin Invest* 87:1–5 (1991).
Schaller, M. D. et al., *J Cell Biol* 130:1181–1187 (1995).
Shattil, S. et al., *Throm and Haemost* 73:1190 (1995).
Shattil, S. J. et al.,*J Biol Chem* 260:11107–11114 (1985).
Smyth, S. S. et al., *Blood* 81:2827–2843 (1993).
Springer, T., *Curr Biol* 4:506–517 (1994).
Tamkun, J. W. et al., *Cell* 46:271–282 (1986).
Tapley, P. et al., *Oncogene* 4:325–333 (1989).
Tcheng, J.E. et al.,*Circulation* 91:2151–2157 (1995).
The EPIC Investigation, *New England Journal of Med.* 330:956–961 (1994).
Vuori, K. et al., *Science* 266:1576–1578 (1994).
Ylanne, J. et al., *J Biol Chem* 270:9550–9557 (1995).
Ylanne, J., et al., *J Cell Biol* 122:223–233 (1993).
Lanza, *Journal of Biological Chemistry*, 265(30):18098–18103 (1990).
Lukashev, *Journal of Biological Chemistry*, 269(28):18311–18314 (1994).

\* cited by examiner

*Primary Examiner*—Christina Y. Chan
*Assistant Examiner*—Gerald R. Ewoldt
(74) *Attorney, Agent, or Firm*—Morgan, Lewis & Bockius LLP

(57) ABSTRACT

The present invention discloses that phosphorylation of cytoplasmic tyrosine residues in the β-subunit of integrins is needed for signal protein association. The invention provides methods of identifying signaling partners involved in integrin mediated signaling, methods of identifying agents which block integrin mediated signaling, methods of using agents which block integrin mediated signaling to modulate biological and pathological processes, and agents which block integrin mediated signaling.

7 Claims, 5 Drawing Sheets

|  |  |  |  |  |  |
|---|---|---|---|---|---|
| GP IIIa (β3) | KlLLtTHDRk | EFAKFEeEra | rAKwdtanNP | LYKeAt⊙Jft | ..........Ni | tYrgt......  ........ |
| β6 | KLLVsfHDRk | EvAKFEaErs | kAKwqtgtNP | LYrgstsTfk | ..........Nv | tYkhrekqkv dlstdc |
| β1 | KLLmlIHDRR | EFAKEEkm | nAkwdtgeNP | iYKsAvtTvv | ..........Np | kYegk......  ........ |
| β5 | KLLVtIHDRR | EFAKFqsErs | rArYemasNP | LYrkpisTht | vdftfnkfNk | sYngtvd...  ........ |
| β2 | KaLThlsDlR | EYrrFEkEkl | ksqwnnd.NP | LFkSAltTvm | ..........Np | kFaes......  ........ |
| β7 | rLsVelyDRR | EYsrFEkEqq | qlnwkqdsNP | LYkSAittTti | ..........Np | rFqeadsptl ........ |
| Cn | KLLV-IHDRR | EFAKFE-E-- | -A-W----NP | LYK-A--T-- | ----------N- | -Y--------  -------- |

FIG. 2

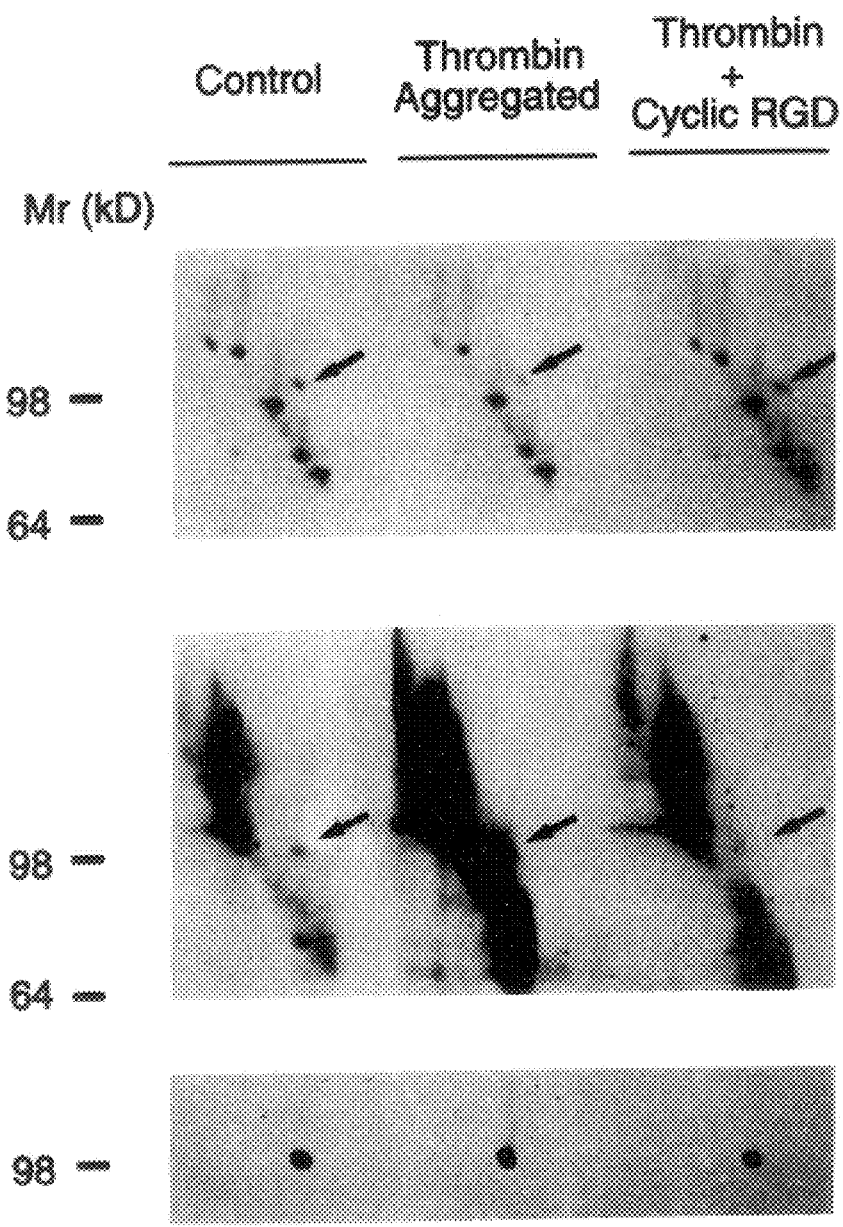
FIG. 3A Coomassie stained
FIG. 3B Anti-ptyr
FIG. 3C Anti-β3

SEQUENCE LISTING

<160> NUMBER OF SEQ ID NOS: 27

<210> SEQ ID NO 1
<211> LENGTH: 23
<212> TYPE: PRT
<213> ORGANISM: Artificial Sequence
<220> FEATURE:
<221> NAME/KEY: MOD_RES
<222> LOCATION: (8)
<223> OTHER INFORMATION: PHOSPHORYLATION
<221> NAME/KEY: MOD_RES
<222> LOCATION: (20)
<223> OTHER INFORMATION: PHOSPHORYLATION
<223> OTHER INFORMATION: Description of Artificial Sequence: Beta 1
       subunit of integrin

<400> SEQUENCE: 1

Asp Thr Gly Glu Asn Pro Ile Tyr Lys Ser Ala Val Thr Thr Val Val
 1               5                  10                  15

Asn Pro Lys Tyr Glu Gly Lys
            20

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Beta 2
      subunit of integrin
<221> NAME/KEY: MOD_RES
<222> LOCATION: (5)
<223> OTHER INFORMATION: PHOSPHORYLATION

<400> SEQUENCE: 2

Asp Leu Arg Glu Tyr Arg Arg Phe Glu Lys Glu Lys Leu Ser Gln Trp
 1               5                  10                  15

Asn Asn Asp Asn Pro Leu Phe Lys Ser Ala Thr
            20                  25

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Beta 3
      subunit of integrin
<221> NAME/KEY: MOD_RES
<222> LOCATION: (8)
<223> OTHER INFORMATION: PHOSPHORYLATION
<221> NAME/KEY: MOD_RES
<222> LOCATION: (20)
<223> OTHER INFORMATION: PHOSPHORYLATION

<400> SEQUENCE: 3

Asp Thr Ala Asn Asn Pro Leu Tyr Lys Glu Ala Thr Ser Thr Phe Thr
 1               5                  10                  15

Asn Ile Thr Tyr Arg Gly Thr
            20

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Beta 5
      subunit of intgerin
<221> NAME/KEY: MOD_RES
<222> LOCATION: (8)
<223> OTHER INFORMATION: PHOSPHORYLATION
<221> NAME/KEY: MOD_RES
<222> LOCATION: (28)
<223> OTHER INFORMATION: PHOSPHORYLATION

<400> SEQUENCE: 4

Glu Met Ala Ser Asn Pro Leu Tyr Arg Lys Pro Ile Ser Thr His Thr
 1               5                  10                  15

Val Asp Phe Thr Phe Asn Lys Phe Asn Lys Ser Tyr Asn Gly Thr Val
            20                  25                  30
    Asp

<210> SEQ ID NO 5
<211> LENGTH: 34
<212> TYPE: PRT
<213> ORGANISM: Artificial Sequence
<220> FEATURE:

```
<223> OTHER INFORMATION: Description of Artificial Sequence: Beta 6
      subunit of integrin
<221> NAME/KEY: MOD_RES
<222> LOCATION: (8)
<223> OTHER INFORMATION: PHOSPHORYLATION
<221> NAME/KEY: MOD_RES
<222> LOCATION: (20)
<223> OTHER INFORMATION: PHOSPHORYLATION

<400> SEQUENCE: 5

Gln Thr Gly Thr Asn Pro Leu Tyr Arg Gly Ser Thr Ser Thr Phe Lys
 1               5                  10                  15

Asn Val Thr Tyr Lys His Arg Glu Lys Gln Lys Val Asp Leu Ser Thr
            20                  25                  30

Asp Cys

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Beta 6
      subunit of integrin
<221> NAME/KEY: MOD_RES
<222> LOCATION: (8)
<223> OTHER INFORMATION: PHOSPHORYLATION
<221> NAME/KEY: MOD_RES
<222> LOCATION: (20)
<223> OTHER INFORMATION: PHOSPHORYLATION

<400> SEQUENCE: 6

Gln Thr Gly Thr Asn Pro Leu Tyr Arg Gly Ser Thr Ser Thr Phe Lys
 1               5                  10                  15

Asn Val Thr Tyr Lys His Arg
            20

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Beta 7
      subunit of integrin
<221> NAME/KEY: MOD_RES
<222> LOCATION: (5)
<223> OTHER INFORMATION: PHOSPHORYLATION
<221> NAME/KEY: MOD_RES
<222> LOCATION: (25)
<223> OTHER INFORMATION: PHOSPHORYLATION

<400> SEQUENCE: 7

Asp Arg Arg Glu Tyr Ser Arg Phe Glu Lys Glu Gln Gln Gln Leu Asn
 1               5                  10                  15

Trp Lys Gln Asp Ser Asn Pro Leu Tyr Lys Ser Ala Ile
            20                  25

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: ITAM
      signalling motif in integrin
<221> NAME/KEY: VARIANT
<222> LOCATION: (2)..(4)
<223> OTHER INFORMATION: X at positions 2 and 3 can be any amino acid;
      X at position 4 is Leu or Ile.

<400> SEQUENCE: 8
```

Tyr Xaa Xaa Xaa
 1

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Immune
      receptor activation motif
<221> NAME/KEY: VARIANT
<222> LOCATION: (2)..(16)
<223> OTHER INFORMATION: X at positions 4 and 16 is Leu or Ile; X at
      positions 2, 3, 5-12, 14 and 15 can be any amino
      acid.

<400> SEQUENCE: 9

Tyr Xaa Xaa Xaa Xaa Xaa Xaa Xaa Xaa Xaa Xaa Tyr Xaa Xaa Xaa
 1               5                  10                  15

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Control
      peptide for signal protein binding studies

<400> SEQUENCE: 10

Asp Thr Ala Asn Asn Pro Leu Tyr Lys Glu Ala Thr Ser Thr Phe Thr
 1               5                  10                  15

Asn Ile Thr Tyr Arg Gly Thr
            20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Control
      peptide for signal protein binding studies

<400> SEQUENCE: 11

Asp Thr Gly Glu Asn Pro Ile Tyr Lys Ser Ala Val Thr Thr Val Val
 1               5                  10                  15

Asn Pro Lys Tyr Glu Gly Lys
            20

<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence: Control
      peptide for signal protein binding studies

<400> SEQUENCE: 12

Glu Met Ala Ser Asn Pro Leu Tyr Arg Lys Pro Ile Ser Thr His Thr
 1               5                  10                  15

Val Asp Phe Thr Phe Asn Lys Phe Asn Lys Ser Tyr Asn Gly Thr Val
            20                  25                  30

Asp

<210> SEQ ID NO 13
<211> LENGTH: 34

```
<212> TYPE: PRT
<213> ORGANISM: Artificial Sequence
<220> FEATURE:
<223> OTHER INFORMATION: Description of Artificial Sequence:  Control
      peptide for signal protein binding studies

<400> SEQUENCE: 13

Gln Thr Gly Thr Asn Pro Leu Tyr Arg Gly Ser Thr Ser Thr Phe Lys
 1               5                  10                  15

Asn Val Thr Tyr Lys His Arg Glu Lys Gln Lys Val Asp Leu Ser Thr
            20                  25                  30

Asp Cys

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence:  Control
      peptide for signal protein binding studies

<400> SEQUENCE: 14

Asp Leu Arg Glu Tyr Arg Arg Phe Glu Lys Glu Lys Leu Ser Gln Trp
 1               5                  10                  15

Asn Asn Asp Asn Pro Leu Phe Lys Ser Ala Thr
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence:  Control
      peptide for signal protein binding studies

<400> SEQUENCE: 15

Asp Arg Arg Glu Tyr Ser Arg Phe Glu Lys Glu Gln Gln Gln Leu Asn
 1               5                  10                  15

Trp Lys Gln Asp Ser Asn Pro Leu Tyr Lys Ser Ala Ile
            20                  25

<210> SEQ ID NO 16
<211> LENGTH: 47
<212> TYPE: PRT
<213> ORGANISM: Homo sapiens
<220> FEATURE:
<223> OTHER INFORMATION: GPIIIa Beta 3 subunit

<400> SEQUENCE: 16

Lys Leu Leu Ile Thr Ile His Asp Arg Lys Glu Phe Ala Lys Phe Glu
 1               5                  10                  15

Glu Glu Arg Ala Arg Ala Lys Trp Asp Thr Ala Asn Asn Pro Leu Tyr
            20                  25                  30

Lys Glu Ala Thr Ser Thr Phe Thr Asn Ile Thr Tyr Arg Gly Thr
        35                  40                  45

<210> SEQ ID NO 17
<211> LENGTH: 58
<212> TYPE: PRT
<213> ORGANISM: Homo sapiens
<220> FEATURE:
<223> OTHER INFORMATION: GPIIIa Beta 6 subunit

<400> SEQUENCE: 17
```

```
Lys Leu Leu Val Ser Phe His Asp Arg Lys Glu Val Ala Lys Phe Glu
 1               5                  10                  15

Ala Glu Arg Ser Lys Ala Lys Trp Gln Thr Gly Thr Asn Pro Leu Tyr
                20                  25                  30

Arg Gly Ser Thr Ser Thr Phe Lys Asn Val Thr Tyr Lys His Arg Glu
            35                  40                  45

Lys Gln Lys Val Asp Leu Ser Thr Asp Cys
            50                  55
```

<210> SEQ ID NO 18
<211> LENGTH: 47
<212> TYPE: PRT
<213> ORGANISM: Homo sapiens
<220> FEATURE:
<223> OTHER INFORMATION: GPIIIa Beta 1 subunit

<400> SEQUENCE: 18

```
Lys Leu Leu Met Leu Ile His Asp Arg Arg Glu Phe Ala Lys Phe Glu
 1               5                  10                  15

Lys Glu Lys Met Asn Ala Lys Trp Asp Thr Gly Glu Asn Pro Ile Tyr
                20                  25                  30

Lys Ser Ala Val Thr Thr Val Val Asn Pro Lys Tyr Glu Gly Lys
            35                  40                  45
```

<210> SEQ ID NO 19
<211> LENGTH: 57
<212> TYPE: PRT
<213> ORGANISM: Homo sapiens
<220> FEATURE:
<223> OTHER INFORMATION: GPIIIa Beta 5 subunit

<400> SEQUENCE: 19

```
Lys Leu Leu Val Thr Ile His Asp Arg Arg Glu Phe Ala Lys Phe Gln
 1               5                  10                  15

Ser Glu Arg Ser Arg Ala Arg Tyr Glu Met Ala Ser Asn Pro Leu Tyr
                20                  25                  30

Arg Lys Pro Ile Ser Thr His Thr Val Asp Phe Thr Phe Asn Lys Phe
            35                  40                  45

Asn Lys Ser Tyr Asn Gly Thr Val Asp
            50                  55
```

<210> SEQ ID NO 20
<211> LENGTH: 46
<212> TYPE: PRT
<213> ORGANISM: Homo sapiens
<220> FEATURE:
<223> OTHER INFORMATION: GPIIIa Beta 2 subunit

<400> SEQUENCE: 20

```
Lys Ala Leu Ile His Leu Ser Asp Leu Arg Glu Tyr Arg Arg Phe Glu
 1               5                  10                  15

Lys Glu Lys Leu Lys Ser Gln Trp Asn Asn Asp Asn Pro Leu Phe Lys
                20                  25                  30

Ser Ala Thr Thr Thr Val Met Asn Pro Lys Phe Ala Glu Ser
            35                  40                  45
```

<210> SEQ ID NO 21
<211> LENGTH: 52
<212> TYPE: PRT
<213> ORGANISM: Homo sapiens
<220> FEATURE:
<223> OTHER INFORMATION: GPIIIa Beta 7 subunit -continued

<400> SEQUENCE: 21

Arg Leu Ser Val Glu Ile Tyr Asp Arg Arg Glu Tyr Ser Arg Phe Glu
 1               5                  10                  15

Lys Glu Gln Gln Gln Leu Asn Trp Lys Gln Asp Ser Asn Pro Leu Tyr
            20                  25                  30

Lys Ser Ala Ile Thr Thr Thr Ile Asn Pro Arg Phe Gln Glu Ala Asp
        35                  40                  45

Ser Pro Thr Leu
        50

<210> SEQ ID NO 22
<211> LENGTH: 52
<212> TYPE: PRT
<213> ORGANISM: Artificial Sequence
<220> FEATURE:
<223> OTHER INFORMATION: Description of Artificial Sequence:  Consensus
      sequence for human GPIIIa Beta subunits
<221> NAME/KEY: NON_CONS
<222> LOCATION: (5)..(51)
<223> OTHER INFORMATION: X at positions 5, 17, 19, 20, 21, 23, 25-28,
      34, 36, 37, 39-48, 50, 51 can be any amino acid.

<400> SEQUENCE: 22

Lys Leu Leu Val Xaa Ile His Asp Arg Arg Glu Phe Ala Lys Phe Glu
 1               5                  10                  15

Xaa Glu Xaa Xaa Xaa Ala Xaa Trp Xaa Xaa Xaa Xaa Asn Pro Leu Tyr
            20                  25                  30

Lys Xaa Ala Xaa Xaa Thr Xaa Xaa Xaa Xaa Xaa Xaa Xaa Xaa Xaa Xaa
        35                  40                  45

Asn Xaa Xaa Tyr
        50

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence:  Proline-
      substituted form of Beta 3 subunit of integrin
<221> NAME/KEY: MOD_RES
<222> LOCATION: (8)
<223> OTHER INFORMATION: PHOSPHORYLATION
<221> NAME/KEY: MOD_RES
<222> LOCATION: (20)
<223> OTHER INFORMATION: PHOSPHORYLATION

<400> SEQUENCE: 23

Asp Thr Ala Asn Asn Pro Leu Tyr Lys Glu Ala Thr Pro Thr Phe Thr
 1               5                  10                  15

Asn Ile Thr Tyr Arg Gly Thr
            20

<210> SEQ ID NO 24
<211> LENGTH: 23
<212> TYPE: PRT
<213> ORGANISM: Artificial Sequence
<220> FEATURE:
<223> OTHER INFORMATION: Description of Artificial Sequence:
      Monophosphorylated form of Beta 3 subunit of
      integrin
<221> NAME/KEY: MOD_RES
<222> LOCATION: (20)
<223> OTHER INFORMATION: PHOSPHORYLATION

<400> SEQUENCE: 24

-continued

```
Asp Thr Ala Asn Asn Pro Leu Tyr Lys Glu Ala Thr Ser Thr Phe Thr
 1               5                  10                  15

Asn Ile Thr Tyr Arg Gly Thr
             20

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence:
      Monophosphorylated form of Beta 3 subunit of
      integrin
<221> NAME/KEY: MOD_RES
<222> LOCATION: (8)
<223> OTHER INFORMATION: PHOSPHORYLATION

<400> SEQUENCE: 25

Asp Thr Ala Asn Asn Pro Leu Tyr Lys Glu Ala Thr Ser Thr Phe Thr
 1               5                  10                  15

Asn Ile Thr Tyr Arg Gly Thr
             20

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:  Motif for
      phosphotyrosine-binding domain

<400> SEQUENCE: 26

Asn Pro Leu Tyr
 1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:  Consensus
      sequence for phosphotyrosine-binding domain

<400> SEQUENCE: 27

Asn Pro Xaa Tyr
```

MODULATION OF INTEGRIN-MEDIATED SIGNAL TRANSDUCTION

RELATED APPLICATION

This application claims priority from U.S. provisional application Ser. No. 60/005,567, filed Oct. 18, 1995, the contents of which are herein incorporated by reference.

FIELD OF THE INVENTION

The present invention relates to the modulation of integrin-mediated signal transduction, particularly signal transduction mediated by GPIIb-IIIa on platelets. The invention relates specifically to the identification of molecules that mediate integrin signaling and to methods of modulating integrin-mediated signaling.

BACKGROUND OF THE INVENTION

Integrins are a family of $\alpha\beta$ heterodimers that mediate adhesion of cells to extracellular matrix proteins and to other cells (Clark et al., *Science* (1995) 268: 233–239). Integrins also participate in signal transduction, as evidenced by either an alteration in adhesive affinity of cell surface integrins in response to cellular activation (termed inside-out signal transduction) or by affecting intracellular signaling pathways following integrin-mediated adhesion (termed outside-in signal transduction). Many biological responses are dependent at least to some extent upon integrin-mediated adhesion and cell migration, including embryonic development, hemostasis, clot retraction, mitosis, angiogenesis, cell migration, inflammation, immune response, leukocyte homing and activation, phagocytosis, bone resorption, tumor growth and metastasis, atherosclerosis, restenosis, wound healing, viral infectivity, amyloid toxicity, programmed cell death and the response of cells to mechanical stress.

The integrin family consists of 15 related known $\alpha$ subunits ($\alpha 1$, $\alpha 2$, $\alpha 3$, $\alpha 4$, $\alpha 5$, $\alpha 6$, $\alpha 7$, $\alpha 8$, $\alpha 9$, $\alpha E$, $\alpha V$, $\alpha IIb$, $\alpha L$, $\alpha M$, and $\alpha X$) and 8 related known $\beta$ subunits ($\beta 1$, $\beta 2$, $\beta 3$, $\beta 4$, $\beta 5$, $\beta 6$, $\beta 7$, and $\beta 8$, Luscinskas et al., *FASEB J* (1994) 8:929–938). Integrin $\alpha$ and $\beta$ subunits are known to exist in a variety of pairings as indicated in FIG. 1. Integrin ligand specificity is determined by the specific pairing of the $\alpha$ and $\beta$ subunits, although some redundancy exists as several of the integrins are known to bind the same ligand. FIG. 2 shows the sequences of the cytoplasmic domains of GPIIb and GPIIIa, including the cytoplasmic domains of other $\alpha$ and $\beta$ subunits, respectively, that have homologous cytoplasmic domains. Most integrins containing the $\beta 1$, $\beta 2$, $\beta 3$, $\beta 5$, $\beta 6$, and $\beta 7$ subunits have been found to transduce signals (reviewed by Hynes, *Cell* (1992) 62:11–25). Integrins are involved in both "inside-out" and "outside-in" signaling events.

Various pathologies associated with integrin-related defects are known. For example, inherited deficiencies of GPIIb-IIIa (also termed $\alpha IIb\beta 3$) content or function have been described (termed Glanzmann's thrombasthenia) and are characterized by platelets that do not bind adhesive proteins and therefore fail to aggregate, resulting in a life-long bleeding diathesis. Inhibitors of the binding of fibrinogen and von Willebrand factor to GPIIb-IIIa have been described and have been found to block platelet aggregation in vitro and to inhibit clinical thrombosis in vivo (The EPIC Investigators, *New England Journal of Med* (1994) 330:956–961; Tcheng, J. E. et al., *Circulation* (1995) 91:2151–2157). Also, leukocyte adhesion deficiency (LAD) results from the absence of a $\beta 2$ subunit.

A. Inside-Out Signaling

Inside-out signal transduction has been observed for $\beta 1$, $\beta 2$, and $\beta 3$ integrins. (Hynes, R. O. *Cell* (1992) 69:11–25; Phillips, D. R. et al., *Cell* (1991) 65:359–362; Smyth, S. S. et al., *Blood* (1993) 81:2827–2843; Ginsberg, M. H. et al., *Thromb Haemostasis* (1993) 70:87–93; Juliano, R. L. et al., *Cell Biol* (1993) 120:577–585; Rouslahti, E., *J Clin Invest* (1991) 87:1–5.

Perhaps the most widely studied integrin that is involved in inside-out signaling is GPIIb-IIIa, the receptor for the four adhesive proteins, fibrinogen, von Willebrand factor, vitronectin and fibronectin, on stimulated platelets (Phillips, D. R. et al., *Blood* (1988) 71:83143). The binding of adhesive proteins to GPIIb-IIIa is required for platelet aggregation and normal hemostasis and is also responsible for occlusive thrombosis in high shear arteries.

GPIIb-IIIa is known to be involved in inside-out signal transduction because GPIIb-IIIa on the surface of unstimulated platelets is capable of recognizing only immobilized fibrinogen. In response to platelet stimulation by agents such as thrombin, collagen and ADP, GPIIb-IIIa becomes a receptor for the four adhesive proteins in the previous paragraph, and the binding of fibrinogen and von Willebrand factor causes platelets to aggregate. A monoclonal antibody has been described which detects the activated, receptor competent state of GPIIb-IIIa, suggesting that the conformation of the receptor competent form of GPIIb-IIIa differs from that of GPIIb-IIIa which does not bind soluble fibrinogen or von Willebrand factor (Shattil, S. J. et al., *J Biol Chem* (1985) 260:11107–11114). It has been postulated that inside-out GPIIb-IIIa signal transduction is dependent on cellular proteins that act to repress or stimulate GPIIb-IIIa activation (Ginsberg, M. H. et al., *Curr Opin Cell Biol* (1992) 4:766–771).

$\beta 2$ integrins on leukocytes also respond to inside-out signal transduction which accounts, for example, for the increased binding activity of LFA-1 on stimulated lymphocytes and the increased binding activity of MAC-1 on stimulated neutrophils (reviewed by Springer, T., *Curr Biol* (1994) 4:506–517).

B. Outside-In Signaling

Most integrins can be involved in outside-in signal transduction as evidenced by observations showing that binding of adhesive proteins or antibodies to integrins affects the activities of many cells, for example cellular differentiation, various markers of cell activation, gene expression, and cell proliferation (Hynes, R. O. *Cell* (1992) 69:11–25). The involvement of GPIIb-IIIa in outside-in signaling is apparent because the binding of unstimulated platelets to immobilized fibrinogen, a process mediated by GPIIb-IIIa, leads to platelet activation and platelet spreading (Kieffer, N. et al., *J Cell Biol* (1991) 113:451–461).

Outside-in signaling through GPIIb-IIIa also occurs during platelet aggregation. Signaling occurs because fibrinogen or von Willebrand factor bound to the activated form of GPIIb-IIIa on the surface of stimulated platelets, coupled with the formation of platelet-platelet contacts, causes further platelet stimulation through GPIIb-IIIa signal transduction. In this manner, binding of adhesive proteins to GPIIb-IIIa can both initiate platelet stimulation or can augment stimulation induced by the other platelet agonists such as ADP, thrombin and collagen. The binding of soluble fibrinogen to GPIIb-IIIa on unstimulated platelets can also be induced by selected GPIIb-IIIa antibodies such as LIBS6 (Huang, M -M. et al., *J Cell Biol* (1993) 122:473–483): although platelets with fibrinogen bound in this manner are not believed to be stimulated, such platelets will aggregate if agitated and will become stimulated following aggregation through GPIIb-IIIa signal transduction.

Outside-in integrin signal transduction results in the activation of one or more cascades within cells. For GPIIb-IIIa, effects caused by integrin ligation include enhanced actin polymerization, increased $Na^+/H^+$ exchange, activation of phospholipases, increased phosphatidyl turnover, increased cytoplasmic $Ca^{++}$, and activation of kinases. Kinases known to be activated include PKC, myosin light chain kinase, src, syk and pp125FAK. Kinase substrates identified include pleckstrin, myosin light chain, src, syk, pp125FAK, and numerous proteins yet to be identified (reviewed in Clark, E. A. et al., *Science* (1995) 268:233–239). Many of these signaling events, including phosphorylations, also occur in response to ligation of other integrins (reviewed in Hynes, R. O. *Cell* (1992) 69:11–25). Although these other integrins have distinct sequences and distinct α-β3 parings that allow for ligand specificity, the highly conserved nature of the relatively small cytoplasmic domains, both between species and between subunits, predicts that related mechanisms will be responsible for the transduction mechanisms of many integrins.

C. Signal Transduction

Despite the numerous observations on the binding of cytoplasmic proteins to GPIIb-IIIa and other integrins, it is not yet known whether the binding of any of these is involved in integrin signal transduction nor is it known what regulates their binding to the integrin. There have been several attempts to determine whether phosphorylation of the cytoplasmic domain of GPIIIa and β1 is responsible for GPIIb-IIIa signal transduction. These studies, discussed below, apparently originated from the suggestion made following the determination of the primary sequence of GPIIIa and β1 which showed that tyrosine 747 on the cytoplasmic domain of GPIIIa (and tyrosine 788 on the cytoplasmic domain of β1) was a possible phosphorylation site as it existed within a motif similar to a tyrosine which exists in the cytoplasmic domains of the epidermal growth factor and insulin receptors which are known phosphorylation sites (Fitzgerald, L. et al., *J Biol Chem* (1987) 262:3936–3939; Tamkun, J. W. et al., *Cell* (1986) 46:271–282).

Nonetheless, the involvement of the cytoplasmic domain of GPIIb-IIIa in integrin signal transduction is inferred from mutagenesis experiments. Deletion of the cytoplasmic domain of GPIIb results in a constitutively active receptor that binds fibrinogen with an affinity equivalent to the wild-type complex, implying that the cytoplasmic tail of GPIIb has a regulatory role (O'Toole, T. E. et al., *Cell Regul* (1990) 1:883–893). Point mutations, deletions and other truncations of GPIIb-IIIa affects the ligand binding activity of GPIIb-IIIa and its signaling response (Hughes, P. E. et al., *J Biol Chem* (1995) 270:12411–12417; Ylanne, J. et al., *J Biol Chem* (1995) 270:9550–9557).

Chimeric, transmembrane proteins containing the cytoplasmic domain of GPIIIa, but not of GPIIb, inhibit the function of GPIIb-IIIa (Chen, Y. -P. et al., *J Cell Biol* (1994) 269:18307–18310), implying that free GPIIIa cytoplasmic domains bind proteins within cells and that this binding is necessary for normal GPIIb-IIIa function. Several proteins have been shown to bind either the transmembrane domains or the cytoplasmic domains of GPIIb or GPIIIa.

CD 9, a member of the tetraspanin family of proteins (Lanza, F. et al., *J Biol Chem* (1991) 266:10638–10645), has been found to interact with GPIIb-IIIa on aggregated platelets. β3-endonexin, a protein identified through two hybrid screening using the cytoplasmic domain of GPIIIa as the "bait", has been found to interact directly and selectively with the cytoplasmic tail of GPIIIa (Shattil, S. et al., *Throm and Haemost* (1995) 73:1190). β3-endonexin shows decreased binding to the GPIIIa cytoplasmic domain containing the thrombasthenic S752-P mutation. It is not yet known whether either of these GPIIIa-binding proteins are involved in signal transduction.

Cytoplasmic proteins that bind to αVβ3 have also been described which may be interacting with the integrin at the GPIIIa cytoplasmic domain sequence. Bartfeld and coworkers (Bartfeld, N. S. et al., *J Biol Chem* (1993) 268:17270–17276) used immunoprecipitation from detergent lysates to show that a MW=190 kDa protein associates with the αVβ3 integrin from PDGF-stimulated 3T3 cells. IRS-1 was found to bind to the αVβ3 integrin following insulin stimulation of Rat-1 cells stably transfected with DNA encoding the human insulin receptor (Vuori, K. et al., *Science* (1994) 266:1576–1578).

β1-containing hybrid proteins also have a dominant negative effect on integrin function implying that β1 integrins also bind cytoplasmic proteins (LaFlamme, S. E. et al., *J Cell Biol* (1994) 126:1287–1298). The importance of the cytoplasmic domain of β1 is underscored by the demonstration that its removal markedly reduces the adhesive activity of the integrin α5β1 (Hyashi, Y. et al., *J Cell Biol* (1990) 110:175–184; Ylanne, J., et al., *J Cell Biol* (1993) 122:223–233). Mutations of defined sequences of the cytoplasmic domain of β1 have been shown to decrease integrin recruitment to adhesion plaques (Reszka, A. A. *J Cell Biol* (1992) 117:1321–1330). Several 11 cytoplasmic domain binding proteins have been described. Otey and coworkers (Otey, C. A. et al., *J Biol Chem* (1993) 268:21193–21197) have used synthetic peptides to map the binding site for α-actinin within the cytoplasmic domain of β1. Talin binding to a peptide corresponding to the cytoplasmic domain of β1 has been observed (Horwitz, A., et al., *Nature* (1986) 320:531–533). Argraves and coworkers (Argraves, W. S. et al., *Cell* (1989) 58:623–629) also used synthetic peptides to show that fibulin bound to the cytoplasmic domain of β1. The $NH_2$-terminal, noncatalytic domain of pp125FAK has been found to directly bind to the cytoplasmic tail of β1 and to recognize integrin sequences distinct from those involved in binding to α-actinin (Schaller, M. D. et al., *J Cell Biol* (1995) 130:1181–1187). Integrin-associated kinase (IAK) is a tyrosine kinase that has been found to bind to the cytoplasmic tail of β1 (Hannigan, G. E. et al., *Nature* (1996) 379:91–96).

In order to determine whether or not GPIIIa was phosphorylated on tyrosine residues as a consequence of platelet activation, the following experiments were performed. GPIIb-IIIa from control and thrombin-stimulated platelets was analyzed for changes in phosphorylation and it was observed that stimulation caused an increase in the phosphorylation of GPIIIa, but that the phosphorylation was primarily on serine, with no detectable phosphorylation of tyrosine (Parise, L. V. et al., *Blood* (1990) 75:2363–2368). Consistent with these findings, a variant of Glanzmann's thrombasthenia has been described where the deficiency of the platelet aggregation response has been attributed to the replacement of a serine residue in the cytoplasmic tail of GPIIIa by a proline residue (Chen, Y. -P. et al., *Proc Natl Acad Sci USA* (1992) 89:10169–10173). This implies that the sequence that occurs for normal GPIIIa is required for GPIIb-IIIa signal transduction, possibly involving the activation of the receptor function.

Other studies have shown that the sequences of the cytoplasmic domains of GPIIIa, β1 and β2 which contain tyrosines are important for normal functioning of GPIIb-IIIa and of other integrins. Substitution of tyrosine 747 by alanine in GPIIIa transfected into CHO cells abolished GPIIIa-mediated cell spreading, blocked the recruitment of GPIIb-IIIa to preestablished adhesion plaques, and decreased the ability of GPIIb-IIIa to mediate internalization of fibrinogen-coated particles (Ylanne, J. et al., *J Biol Chem* (1995) 270:9550–9557). Additional experiments in this study showed further that substitution of tyrosine 759 by alanine decreased cell spreading and the recruitment of GPIIb-IIIa to plaques, while deletion of the carboxy terminal pentapeptide that contains this sequence had an even more pronounced effect on the function of the integrin. These authors concluded integrin-mediated cell spreading does not occur because the factors that are absolutely required for integrin-mediated cell spreading cannot bind either the GPIIIa truncated at residue 757 or to the integrin with tyrosine 747 on GPIIIa substituted by alanine. Point mutations in homologous domains in $\beta$1- and $\beta$2-containing integrins also suggest that these domains are functional as these mutations affect integrin-cytoskeletal interactions (Reszka, A. A. et al., *J Cell Biol* (1992) 117:1321–1330) and integrin activation (Hibbs, M. L. et al., *J Exp Med* (1991) 174:1227–1238), respectively. Similarly, an NPXY SEQ ID NO: 27 motif in the integrin $\beta$3 cytoplasmic subunit tail appears necessary for melanoma cell migration (Filardo, E. J. et al., *J Cell Biol* (1995) 130:441–450; O'Toole, T. E. *J Biol Chem* (1995) 270:8553–8558).

Some commentators have suggested that the phosphorylation of isolated cytoplasmic tyrosine residues was implicated in signal transduction. For example, GPIIb and IIIa isolated from human platelets were reported to serve as substrates for $PP_{60}^{c-src}$ (Findik, D. et al, *FEBS* (1990) 262:1–4). The tyrosine(s) on the cytoplasmic domain of GPIIIa also have been found to be an in vitro substrate for src (Elmore, M. A. et al., *FEBS* (1990) 269:283–287), but it has not been demonstrated that src phosphorylates GPIIIa in vivo.

Others have reported that these tyrosine residues are not phosphorylated during normal integrin function (Hillery, C. A. et al., *J Biol Chem* (1991) 266:14663–14669). Thus, neither of the GPIIIa containing integrins, GPIIb-IIIa or $\alpha V\beta 3$, are believed to be phosphorylated on tyrosine.

Tyrosine phosphorylation of $\beta$1 has been observed, however, but only in cells overexpressing vSrc (Hirst, R. et al., *PNAS USA* (1986) 83:6470–6474). $\beta$1 phosphorylation coincides with a decrease in the ability of the $\alpha 5\beta 1$ integrin to mediate cell adhesion (Horwitz, A. et al., *Nature* (1986) 320:531–533) and a decrease in the ability of this integrin to localize to focal adhesion plaques (Johansson, M. W. et al., *J Cell Biol* (1994) 126:1299–1309). Increased phosphorylation of the cytoplasmic domain of $\beta$1 may decrease the binding of talin (Tapley, P. et al., *Oncogene* (1989) 4:325–333). The available data on $\beta$1 integrins suggest that tyrosine phosphorylation of $\beta$1 has a negative effect on its function and that tyrosine phosphorylation of $\beta$1 may be associated with a transformation phenotype. Similarly, phosphorylation of two conserved tyrosines in the cytoplasmic domain of the integrin $\beta_{ps}$ subunit was found to be unnecessary for developmental functions in Drosophila (Grinblat, Y. et al., *Development* (1994) 120:91–102).

Integrin binding to adhesive proteins and integrin signal transduction have a wide variety of physiological roles, as identified above. Enhanced signaling through integrins allows for increased cell adhesion and activation of intracellular signaling molecules which causes enhanced cell mobility and growth, enhanced cell responsiveness, and modulations in morphological transformations. Although integrins responsible for cellular function have been described and signaling events are beginning to be elucidated, the mechanism by which integrins transduce signals remains to be determined. Identification of the event (s) which allow for integrin interactions with cytoplasmic signaling molecules will greatly enhance the understanding of integrin function and will provide for agents which can modulate integrin function. Such agents will be useful for the treatment and diagnosis of a wide spectrum of pathologies, including the processes described above. The present invention describes the event which allows for the interaction in vivo of GPIIb-IIIa with intracellular signaling molecules and peptide structures which can be used to modulate these signaling events.

SUMMARY OF THE INVENTION

The present invention is based in part on the discovery that tyrosine residue in the cytoplasmic domain of $\beta$-subunits of integrins require phosphorylation in vivo for signal transduction. Signaling partners become associated with phosphorylated cytoplasmic domains while no association occurs with integrin subunits lacking phosphorylated cytoplasmic tyrosine residues.

Based on these discoveries, the present invention provides phosphorylated peptide fragments of the cytoplasmic domains of integrin $\beta$-subunits. These peptides can be used to isolate integrin signaling proteins and complexes, as agents to reduce the association of signaling partners with integrins, and as targets for the development of pharmaceutical agents.

The present invention further provides methods for reducing or blocking the association of an integrin with a cytoplasmic signaling partner. Specifically, the association of an integrin with a cytoplasmic signaling partner can be blocked or reduced by contacting an integrin having a phosphorylated tyrosine in the cytoplasmic domain of the $\beta$-subunit, or a fragment thereof comprising the phosphorylated cytoplasmic domain, with an agent which blocks the binding of the signaling partner to the integrin. The method can use an agent which binds to the cytoplasmic domain of the integrin or an agent which binds to the signaling partner.

Blocking integrin/signaling partner associations can be used to modulate biological and pathological processes which require an integrin mediated signal. Such methods and agents can be used to modulate cellular attachment or adhesion to a substrate or another cell, cellular migration, cellular proliferation and cellular differentiation. Pathological processes involving these action include thrombosis, inflammation, tumor metastasis, wound healing and others noted above.

The present invention further provides methods for isolating integrin signaling partners. Integrin signaling partners are isolated using a tyrosine phosphorylated cytoplasmic domain of a $\beta$-subunit as a capture probe. Specifically, a peptide containing the phosphorylated cytoplasmic tyrosine of an integrin is mixed with an extract prepared from an integrin expressing cell under condition which allow association of the $\beta$-subunit fragment with a signaling partner. Non-associated cellular constituents are removed from the mixture and the signaling partner is released from the $\beta$-subunit probe. Signaling partners isolated by this method are useful in preparing antibodies and also serve as targets for drug development.

The present invention further provides methods to identify agents which can block or modulate the association of an integrin with a signaling partner. Specifically, an agent can be tested for the ability to block or reduce or otherwise modulate the association of an integrin with a signaling partner by incubating a peptide comprising the phosphorylated cytoplasmic domain of the β-subunit of an integrin with a signaling partner and a test agent, and determining whether the test agent blocks or reduces the binding of the signaling partner to the integrin peptide. Agonists, antagonists and other modulators expressly are contemplated.

The present invention further provides methods of reducing the severity of pathological processes which require integrin mediated signaling. Since phosphorylation is required for the association of integrins with cytoplasmic signaling partners, agents which block integrin/signaling partner association, agents which block tyrosine phosphorylation, and agents which dephosphorylate phosphorylated tyrosines can be used in therapeutic methods.

BRIEF DESCRIPTION OF THE DRAWINGS

FIG. 2 shows cytoplasmic domains of various integrin subunits SEQ ID NO: 16–22.

FIGS. 3A–3B show tyrosine phosphorylation of the integrin GPIIIa (β3) subunit.

FIGS. 4A–4C show in vitro phosphorylation of GPIIIa (β3).

DETAILED DESCRIPTION OF THE PREFERRED EMBODIMENT

I. General Description

Figure 1:
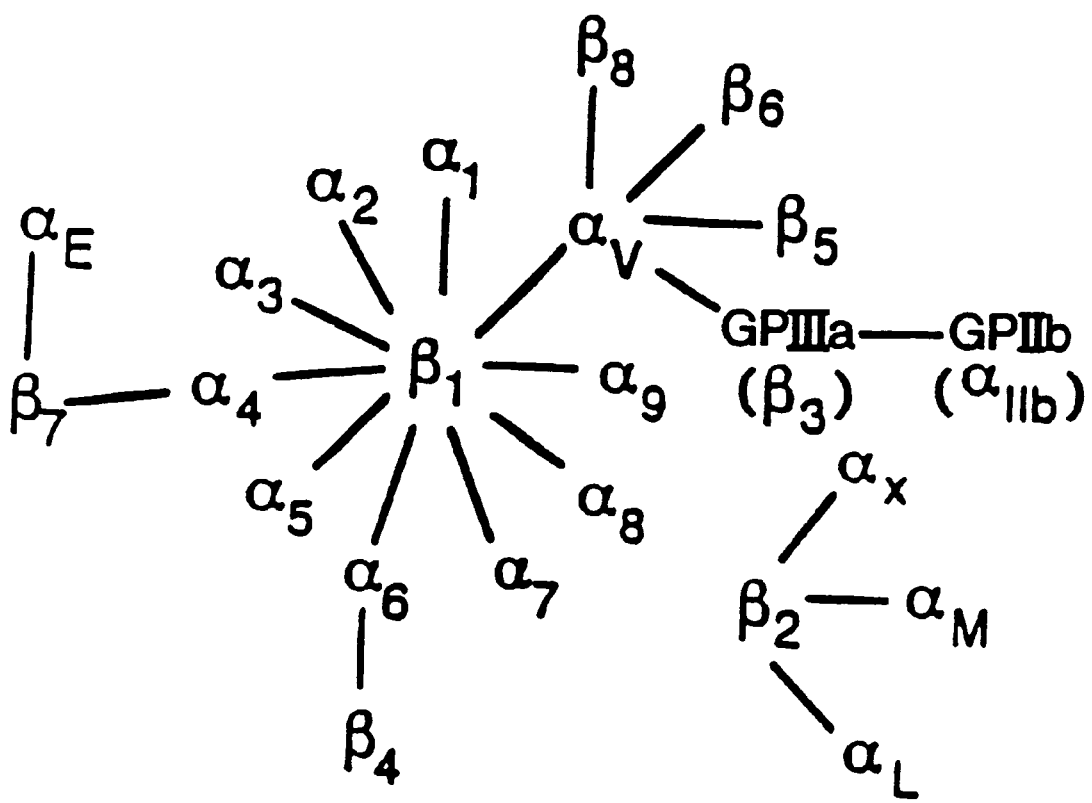
FIG. 1 shows pairing of α and β integrin subunits.

The present invention is based in part on identifying the mechanism by which integrins are modified so that they can interact with signaling proteins and signaling complexes. In the following Examples, data are provided showing that GPIIIa unexpectedly is phosphorylated at a tyrosine residue in the cytoplasmic domain during platelet aggregation and that src and fyn may be the responsible kinases. The high degree of sequence and motif structure homology found around the phosphorylation site of the cytoplasmic domain of GPIIIa when compared to the corresponding structure/sequences found in other β subunits, particularly β1, β5, β6 and β7 subunits, predicts that tyrosinyl phosphorylation is a widely utilized mechanism for regulating signal protein association within the integrin family of receptors.

The present invention is further based on identifying how to modify fragments of the β subunit of an integrin so that they interact with integrin associated signaling proteins.

In the Examples, phosphorylated peptides corresponding to part of the cytoplasmic domain of an integrin, for example, GPIIIa, are demonstrated to bind cytoplasmic signaling proteins and complexes while the unphosphorylated peptide did not. The phosphorylated peptides also bound to additional proteins of unknown identity. The phosphorylated peptides can be used as an agent, or serve as a target for agents, which can be used to inhibit integrin mediated signaling, for example to inhibit biological processes requiring GPIIb-IIIa or αVβ3 signal transduction. Further, phosphorylated peptides corresponding to the homologous sequences in the β1, β5, β6 and β7 subunits, or mimics of these sequences, can be used as an agent or serve as a target for agents which can be used to inhibit signaling for other integrins containing these β subunits.

The present invention is further based on the development of methods for isolating integrin signaling proteins. Phosphorylated peptide probes based on the cytoplasmic domain of integrin β subunits are used as capture probes to isolate integrin associated signaling proteins. Dominant negative proteins, DNAs encoding these proteins, antibodies to these signaling proteins, peptide fragments of these proteins or mimics of these proteins may be introduced into cells to affect integrin function. Additionally, these proteins provide a novel target for screening of synthetic small molecules and combinatorial or naturally occurring compound libraries to discover novel therapeutics to regulate integrin function.

Utilizing these observations, the present invention provides methods of identifying tyrosine phosphorylation sites on integrin β subunits, methods of identifying cytoplasmic signaling partners which associate with phosphorylated β subunits, methods to assay for integrin mediated signaling, methods to identify agents which block integrin mediated cytoplasmic signaling, and therapeutic uses for agents which modulate integrin mediated cytoplasmic signaling.

II. Specific Embodiments

A. Tyrosine Phosphorylation Sites in the Cytoplasmic Domain of Integrin β Subunits In the Examples, data are presented which demonstrate that the tyrosine residues found within the cytoplasmic domain of the β subunit of an integrin are phosphorylated in vivo. Upon phosphorylation, cellular signaling partners found within the cytoplasm of the integrin-expressing cell become associated with the β subunit. These signaling partners do not become associated with cytoplasmic domains of β subunits which lack a phosphorylated tyrosine. Based on these observations, one aspect of the present invention provides, as examples, the amino acid sequence of the cytoplasmic domain of integrin β subunits which, upon phosphorylation, become associated with signaling proteins and complexes.

In detail, the present invention provides six β subunit peptides possessing a tyrosine residue which can be phosphorylated by a cellular tyrosine kinase. The cytoplasmic domain sequences of each of the characterized β subunits, with the corresponding phosphorylation site identified, are:

β1 subunit: NH-D-T-G-E-N-P-I-Y($PO_3$)-K-S-A-V-T-T-V-V-N-P-K-Y($PO_3$)-E-G-K-COOH (SEQ ID NO: 1)

β2 subunit: NH-D-L-R-E-Y($PO_3$)-R-R-F-E-K-E-K-L-S-Q-W-N-N-D-N-P-L-F-K-S-A-T-COOH (SEQ ID NO: 2)

β3 subunit: NH-D-T-A-N-N-P-L-Y($PO_3$)-K-E-A-T-S-T-F-T-N-I-T-Y($PO_3$)-R-G-T-COOH (SEQ ID NO: 3)

β5 subunit: NH-E-M-A-S-N-P-L-Y($PO_3$)-R-K-P-I-S-T-H-T-V-D-F-T-F-N-K-F-N-K-S-Y($PO_3$)-N-G-T-V-D-COOH (SEQ ID NO: 4)

β6 subunit: NH-Q-T-G-T-N-P-L-Y($PO_3$)-R-G-S-T-S-T-F-K-N-V-T-Y($PO_3$)-K-H-R-E-K-Q-K-V-D-L-S-T-D-C-COOH (SEQ ID NO: 5) or
NH-Q-T-G-T-N-P-L-Y($PO_3$)-R-G-S-T-S-T-F-K-N-V-T-Y($PO_3$)-K-H-R-COOH (SEQ ID NO: 6)

β7 subunit: NH-D-R-R-E-Y($PO_3$)-S-R-F-E-K-E-Q-Q-Q-L-N-W-K-Q-D-S-N-P-L-Y($PO_3$)-K-S-A-I-COOH (SEQ ID NO: 7)

The present invention provides these peptides, as well as those of the foregoing section of this specification and the peptides disclosed in the examples that follow, as well as homologous portions of allelic variants of the corresponding integrins, and conservative amino acid substitutions of these peptides. As used herein, an allelic variant refers to a naturally occurring β integrin (or more specifically to its cytoplasmic domain) having a different amino acid sequence than that specifically recited above. Allelic variants, though possessing a different amino acid sequence than those recited above, will still have the requisite phosphorylatable tyrosine residue recognized by the integrin signaling partner and will function to associate or interact with this partner as part of the relevant signaling cascade.

As used herein, a conservative amino acid substitution refers to alterations in the amino acid sequence which do not adversely effect the peptide. A substitution is said to adversely effect the peptide when the altered sequence prevents the phosphorylation of the peptide or the ability of the phosphorylated peptide to associate with a signaling partner. For example, the overall charge, structure or hydrophobic/hydrophilic properties of the peptide can be altered without adversely effecting the peptide. Accordingly, the amino acid sequence of the above peptides can be altered, for example to render the peptide more hydrophobic or hydrophilic, without adversely effecting the ability of the peptide to become phosphorylated or the ability of the phosphorylated peptide to associate with a signaling partner.

Ordinarily, the peptides and analogs thereof claimed herein will have an amino acid sequence having at least 75% amino acid sequence identity with the disclosed peptides from the cytoplasmic domains of β integrins (such as those disclosed in Examples 2 and 4–8), more preferably at least 80%, even more preferably at least 90%, and most preferably at least 95%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. None of N-terminal, C-terminal or internal extensions, deletions, or insertions into the peptide sequence shall be construed as affecting homology.

Thus, the claimed peptides and analog molecules that are the subject of this invention include molecules having the sequences disclosed; fragments thereof having a consecutive sequence of at least about 3, 5, 10 or 15 amino acid residues from the corresponding cytoplasmic domains of β integrins; amino acid sequence variants of such sequences wherein an amino acid residue has been inserted N- or C-terminal to, or within, the disclosed sequences or their fragments as defined above; and amino acid sequence variants of the disclosed sequences or their fragments as defined above which have been substituted by another residue. Contemplated polypeptides include those containing predetermined mutations by, e.g., homologous recombination, site-directed or PCR mutagenesis, and the corresponding cytoplasmic domain polypeptides of other animal species, including but not limited to rabbit, rat, murine, porcine, bovine, ovine, equine and non-human primate species, and the alleles or other naturally occurring variants of the cytoplasmic domains of the integrins of the foregoing species and of human sequences; derivatives wherein the peptides or their fragments have been covalently modified, by chemical, enzymatic, or other appropriate means, to attach a moiety other than a naturally occurring amino acid (for example a detectable moiety such as an enzyme or radioisotope); glycosylation variants (insertion of a glycosylation site or deletion of any glycosylation site by deletion, insertion or substitution of appropriate amino acid); and soluble forms as well as irreversibly phosphorylated forms.

The novel proteins and peptides of the present invention are preferably those which share a common biological activity with the disclosed peptides, including but not limited to being phosphorylated by tyrosine kinases that phosphorylate native cytoplasmic domains of β integrins, interactions with signaling partners of β integrin cytoplasmic domains, other effector or receptor function or cross-reactive antigenicity. Such fragments and variants exclude any β integrin cytoplasmic domain peptides heretofore made public, including any known protein or polypeptide of any animal species, which is otherwise anticipatory under 35 U.S.C. §102 as well as polypeptides obvious over such known protein or polypeptides under 35 U.S.C. §103.

As described below, these peptides can be used: 1) to identify and isolate integrin signaling partners, 2) in methods to identify agents which block the association of an integrin with a signaling partner, 3) as a target to assay for integrin mediated signaling, and 4) as a therapeutic agent to block the association of an integrin with a signaling partner.

Nucleic acids encoding the foregoing peptides also are contemplated as part of the present invention. For purposes of this invention, "nucleic acid" is defined as RNA or DNA that encodes a peptide as defined above, or is complementary to nucleic acid sequence encoding such peptides, or hybridizes to such nucleic acid and remains stably bound to it under stringent conditions, or encodes a polypeptide sharing at least 75% sequence identity, preferably at least 80%, and more preferably at least 85%, with the peptide sequences. It is typically at least about 9 nucleotides in length, and specifically contemplated are genomic DNA, cDNA, mRNA and antisense molecules, as well as nucleic acids based on an alternative backbone or including alternative bases whether derived from natural sources or synthesized. Such hybridizing or complementary nucleic acid, however, is defined further as being novel and unobvious over any prior art nucleic acid including that which encodes, hybridizes under stringent conditions, or is complementary to nucleic acid encoding a known peptide, according to the present invention.

"Stringent conditions" are those that (1) employ low ionic strength and high temperature for washing, for example, 0.015M NaCl/0.0015M sodium titrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5× SSC (0.75M NaCl, 0.075 M sodium citrate), 50 mM sodium phosphate (pH 6.8), 0.1% sodium pyrophosphate, 5 × Denhardt's solution, sonicated salmon sperm DNA (50 μg/ml), 0.1% SDS, and 10% dextran sulfate at 42° C., with washes at 42° C. in 0.2× SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

B. Methods to Identify Integrin Cytoplasmic Signaling Partners

Another embodiment of the present invention provides methods for use in isolating and identifying cytoplasmic signaling partners of integrins. Specifically, an integrin containing a β subunit which is phosphorylated on a cytoplasmic tyrosine residue, or a fragment thereof containing the phosphorylated cytoplasmic tyrosine residue, can be used to identify signaling partners from cells which express integrins.

In detail, an integrin containing a β subunit which is phosphorylated on a cytoplasmic tyrosine residue, or a peptide containing the phosphorylated cytoplasmic tyrosine of the β subunit, is mixed with an extract or fraction of a cell which expresses an integrin under conditions which allow the association of a signaling partner with the phosphorylated integrin or peptide. After mixing, peptides that have become associated with a signaling partner are separated from the mixture. The signaling partner that bound the phosphorylated integrin or peptide can then be removed and further analyzed.

Any integrin which contains a phosphorylated tyrosine in the cytoplasmic domain of the β subunit can be used for identifying and isolating an integrin cytoplasmic signaling partner. These particularly include the β1, β2, β3, β5, β6, β7 and β8 subunits, but other β subunits are contemplated. These particularly exclude β subunits in which the phosphorylated tyrosine is followed by an isoleucine or leucine in an ITAM motif (YXXI/L SEQ ID NO. 8). For example, the large β4 cytoplasmic domain contains an ITAM motif and is excluded from the scope of the present invention.

To identify and isolate a signaling partner, the entire intact integrin heterodimer, containing an α subunit and β subunit, can be used. Alternatively, an isolated β subunit or a fragment of the β subunit containing the phosphorylated cytoplasmic tyrosine residue can be used. In a preferred embodiment, a synthetic peptide corresponding to the cytoplasmic domain of the β subunit is used. Such a peptide can be of any length so long as it contains the phosphorylated cytoplasmic tyrosine residue.

As used herein, a cellular extract refers to a preparation or fraction which is made from a lysed or disrupted cell. The preferred source of cellular extracts will be cells which naturally express integrins. Examples of such cells include, but are not limited to platelets and leukocytes. The Examples below demonstrate the use of extracts of platelets to identify signaling partners which bind the GPIIIa subunit.

A variety of methods can be used to obtain an extract of a cell. Cells can be disrupted using either physical or chemical disruption methods. Examples of physical disruption methods include, but are not limited to, sonication and mechanical shearing.

Examples of chemical lysis methods include, but are not limited to, detergent lysis and the enzyme lysis. A skilled artisan can readily adapt methods for preparing cellular extracts in order to obtain extracts for use in the present methods. In Example 1, the detergents NP-40 or Brij 96 were used to generate platelet extracts.

The cellular extract can be prepared from cells which have been freshly isolated from a subject or from cells or cell lines which have been cultured. In addition, the extract can be prepared from cells which are either in a resting state or from cells which have been activated. A variety of agents can be used to activate a cell. The selection of an activating agent will be based on the cell type used. For example, thrombin, collagen or ADP can be used to activate platelets while PMA can be used to activate leukocytes.

Once an extract of a cell is prepared, the extract is mixed with the integrin, or peptide/subunit containing the phosphorylated cytoplasmic tyrosine, under conditions in which association of the phosphorylated subunit with the signaling partner can occur. A variety of conditions can be used, the most preferred being conditions which closely resemble conditions found in the cytoplasm of an integrin-expressing cell. Features such as osmolarity, pH, temperature, and the concentration of cellular extract used, can be varied to optimize the association of the integrin with the signaling partner.

After mixing under appropriate conditions, the integrins or integrin peptides are separated from the mixture. A variety of techniques can be utilized to separate the mixture. For example, antibodies specific to the integrin peptide can be used to immunoprecipitate the integrin and associated signaling partner. Alternatively standard chemical separation techniques such as chromatography and density/sediment centrifugation can be used.

In the examples below, a biotin moiety is linked to the synthetic peptide containing the phosphorylated cytoplasmic tyrosine residue. After mixing, the peptide and associated proteins are separated from the mixture using avidin or biotin-specific antibodies.

After removing nonassociated cellular constituents found in the extract, the signaling partner can be dissociated from the integrin/signaling partner pair using conventional methods. For example, dissociation can be accomplished by altering the salt concentration or pH of the mixture.

To aid in separating associated integrin/signaling partners pairs from the mixed extract, the β subunit peptide can be immobilized on a solid support. For example, a peptide corresponding to the cytoplasmic domain of β3 integrin can be attached to a nitrocellulose matrix or acrylic beads. Attachment of the integrin peptide to a solid support aids in separating the peptide/signaling partner pair from other constituents found in the extract.

The identified signaling partners can be either a single protein or a complex made up of two or more proteins. In the examples below, a peptide containing the GPIIIa cytoplasmic domain was used to purify a previously uncharacterized 230 kD protein. In addition, this peptide was used to isolate a signaling complex containing the shc and grb2 proteins.

C. Use of Isolated Signaling Partners

Once isolated, the integrin signaling partners obtained using the above described methods, can be used for a variety of purposes. The signaling partner can be used to generate antibodies which bind to the signaling partner using techniques known in the art.

Antibodies which bind an integrin signaling partner can be used to assay integrin signaling, as a therapeutic agent to modulate a biological or pathological process mediated by integrin signaling, or to purify the signaling partner. These uses are described in detail below.

D. Methods to Identify Agents That Block Integrin Cytoplasmic Signaling Partner Interactions Another embodiment of the present invention provides methods for identifying agents which reduce or block the association of an integrin with a cytoplasmic signaling partner. Specifically, an integrin, a β subunit of an integrin, or a peptide containing the phosphorylated cytoplasmic tyrosine of a β subunit, is mixed with a cellular extract in the presence and absence of an agent to be tested. After mixing under conditions which allow association of the integrin or peptide with a signaling partner, the two mixtures are analyzed and compared to determine if the agent reduced or blocked the association of the integrin or peptide with the signaling partner. Agents which block or reduce the association of an integrin with a signaling partner will be identified as decreasing the amount of association present in the sample containing the tested agent.

As used herein, an agent is said to reduce or block integrin/cytoplasmic signaling partner association when the presence of the agent decreases the extent to which or prevents the signaling partner from becoming associated with an integrin or integrin peptide fragment containing the phosphorylated cytoplasmic tyrosine residue. One class of agents will reduce or block the association by binding to the signaling partner while another class of agents will reduce or block the association by binding to the cytoplasmic domain of the β integrin.

The integrin peptide fragment containing the phosphorylated cytoplasmic tyrosine residue used in this method can either be the entire isolated β subunit, or a fragment of the β subunit which contains the phosphorylated cytoplasmic tyrosine residues. In some of the examples that follow, a synthetic peptide spanning the cytoplasmic domain of GPIIIa is used.

The signaling partner used in the above assay can either be a fully characterized protein or can be a partially characterized protein which has been identified as being present in a cellular extract. It will be apparent to one of ordinary skill in the art that so long as the signaling partner has been characterized by an identifiable property, e.g., molecular weight, the present assay can be used.

Agents which are assayed in the above method can be randomly selected or rationally selected or designed. As used herein, an agent is said to be randomly selected when the agent is chosen randomly without considering the specific sequences involved in the association of the integrin with the signaling partner. An example of randomly selected agents is the use of a chemical library or a peptide combinatorial library.

As used herein, an agent is said to be rationally selected or designed when the agent is chosen on a nonrandom basis which takes into account the sequence of the target site and/or its conformation in connection with the agent's action. As described above, there are two sites of action for agents which block integrin/signaling partner interaction: the phosphorylated cytoplasmic domain of the β subunit or the signaling partner. Agents can be rationally selected or rationally designed by utilizing the peptide sequences which make up the contact sites of the integrin/signaling partner pair. For example, a rationally selected peptide agent can be a peptide whose amino acid sequence is identical to the phosphorylated cytoplasmic domain of the integrin. Such an agent will reduce or block the association of the integrin with the signaling partner by binding to the signaling partner.

The agents of the present invention can be peptides, small molecules, vitamin derivatives, as well as carbohydrates. A skilled artisan can readily recognize that there is no limit as to the structural nature of the agents of the present invention.

One class of agents of the present invention are peptide agents whose amino acid sequences were chosen based on the amino acid sequence of the cytoplasmic domain of the β subunit of a particular integrin. Such a peptide agent can be modified to prevent dephosphorylation of the tyrosine residue using techniques which are well known in the art.

The nomenclature used to describe the peptide agents follows the conventional practice where the N-terminal amino group is assumed to be to the left and the carboxy group to the right of each amino acid residue in the peptide. In the amino acid sequences representing agents of selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid. In the specific peptides shown in the present application, the L-form of any amino acid residue having an optical isomer is intended. All of the peptide agents of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6C. In all of the peptides of the invention, one or more amide linkages (—CO-NH-) may optionally be replaced with another linkage which is an isostere such as —$CH_2NH$—, —$CH_2S$—, —$CH_2CH_2$, —CH=CH— (cis and trans), —$COCH_2$—, —CH(OH)$CH_2$— and —$CH_2SO$—. This replacement can be made by methods known in the art. The following references describe preparation of peptide analogs which include these alternative-linking moieties: Spatola, A. F., *Vega Data* "Peptide Backbone Modifications" (general review) (1983) 1(3); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—$CH_2NH$—, —$CH_2CH_2$—); Spatola, A. F., et al., *Life Sci* (1986) 38:1243–1249 (—$CH_2$—S); Hann, M. M., *J Chem Soc Perkin Trans I* (1982) 307–314 (—CH—CH—, cis and trans); Almquist, R. G., etal., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Application EP 45665 (1982) CA:97:39405 (—CH(OH)$CH_2$-); Holladay, M. W., et al., *Tetrahedron Lett* (1983) 24:4401–4404 (—C(OH)$CH_2$—); and Hruby, V. J., *Life Sci* (1982) 31:189–199 (—$CH_2$—S—).

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of the phosphorylated cytoplasmic domain of an integrin or with an integrin signaling partner. Antibody agents are obtained by immunization of suitable mammalian subjects with peptides containing as antigenic regions those portions of the phosphorylated cytoplasmic domain or signaling partner intended to be targeted by the antibodies. Critical regions include the contact sites involved in the association of the integrin with a signaling partner.

Antibody agents are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a Cys residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the integrin or signaling partner itself. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of $F(ab')_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin.

The antibodies thus produced are useful not only as modulators of the association of an integrin with a signaling partner, but are also useful in immunoassays for detecting integrin mediated signaling and for the purification of integrin-associated signaling proteins.

E. Uses for Agents that Block the Association of an Integrin with a Signaling Partner As provided in the Background section, integrins play important roles in intracellular signaling, cellular attachment, cellular aggregation and cellular migration. Agents which reduce or block the interactions of an integrin with a cytoplasmic signaling partner can be used to modulate biological and pathologic processes associated with integrin function and activity.

In detail, a biological or pathological process mediated by an integrin can be modulated by administering to a subject an agent which blocks the interaction of an integrin with a cytoplasmic signaling partner.

As used herein, a subject can be any mammal, so long as the mammal is in need of modulation of a pathological or biological process mediated by an integrin. The term "mammal" is meant an individual belonging to the class Mammalia. The invention is particularly useful in the treatment of human subjects.

As used herein, biological or pathological process mediated by an integrin refers to the wide variety of cellular events in which an integrin binds a substrate producing an intracellular signal. Examples of biological processes include, but are not limited to, cellular attachment or adhesion to substrates and other cells, cellular aggregation, cellular migration, cell proliferation, and cell differentiation.

Pathological processes refers to a category of biological processes which produce a deleterious effect. For example, thrombosis is the deleterious attachment and aggregation of platelets while metastasis is the deleterious migration of tumor cells. These pathological processes can be modulated using agents which reduce or block integrin/signaling partner association.

As used herein, an agent is said to modulate a pathological process when the agent reduces the degree or severity of the process. For example, an agent is said to modulate thrombosis when the agent reduces the attachment or aggregation of platelets.

1. Biological and Pathological process mediated by Integrins containing the $\beta 1$ subunit:

A number of different $\alpha$ subunits can combine with the $\beta 1$ subunit. These integrins form a group of proteins known as VLA (very late antigens) since their appearance on certain cell types is upregulated often hours to days post-activation.

$\alpha 1 \beta 1$ (VLA-1) binds both collagen and laminin and is present on a number of cell types, including smooth muscle cells, monocytes and activated T lymphocytes. This integrin plays a role in certain human intestinal inflammatory diseases (MacDonald, T. T. et al., *J Clin Path* (1990) 43:313–315).

$\alpha 2 \beta 1$ (VLA-2) also binds collagen and has a widespread cellular distribution.

It is present on both B and T lymphocytes, fibroblasts, endothelial cells and platelets (Giltay, J. C. et al., *Blood* (1989) 73:1235–1241). This integrin plays an important role in wound healing (Schiro, J. A. et al., *Cell* (1991) 67:403–410).

$\alpha 3 \beta 1$ (VLA-3) binds multiple ligands including laminin and collagen. Its cellular distribution is also broad and this integrin is involved in cell-cell adhesion (Kaufman, R. et al., *J CellBiol* (1989) 109:1807–1815)

$\alpha 4 \beta 1$ (VLA-4) binds fibronectin and VCAM-1, with its expression being restricted mostly to cells of the immune system.

$\alpha 5 \beta 1$ (VLA-5) also functions as a fibronectin receptor and has a wide cellular distribution.

$\alpha 6 \beta 1$ (VLA-6) mediates adhesion to laminin and again is widely distributed.

These latter four integrins have been shown to act as co-stimulatory receptors for T lymphocytes which have been partially activated by T cell receptor stimuli, and a number of the $\beta 1$ integrins have been shown to have outside-in signaling (reviewed in Hynes, R. O. *Cell* (1992) 69:11–25).

2. Biological and Pathological processes mediated by Integrins containing the $\beta 2$ subunit:

The $\beta 2$ subunit can pair with three different $\alpha$ subunits, namely $\alpha L$, $\alpha M$ and $\alpha X$. All three of these integrins are expressed mainly in cells of the immune system and have been shown to play roles in inflammatory processes. Patients exist who lack the $\beta 2$ subunit (termed LAD, leukocyte adhesion deficiency) and these patients show an increased susceptibility to bacterial infections, chronic granulocytosis and lack of pus formation (reviewed in Anderson, D. C. et al., *Ann Rev Med* (1987) 38:175–194).

$\alpha L \beta 2$ (LFA-1, leukocyte function associated antigen 1) is found on lymphocytes, granulocytes, monocytes and macrophages. Its expression levels are increased on memory T cells. This integrin functions in mediating the binding of leukocytes to the epithelium during inflammatory responses, a process that involves its binding to the ligand ICAM-1 (intracellular adhesion molecule 1). It is also involved in a number of the immune functions carried out by T cells, e.g., adhesion of cytotoxic T cells to their targets (reviewed in Larson, R. S. et al., *Immunol Rev* (1990) 114:181–217).

$\alpha M \beta 2$ (Mac-1) found on monocytes, macrophages, granulocytes and NK cells. This integrin mediates adherence to both matrix and cell surface proteins. Its ligands include fibrinogen, factor X, C3bi and ICAM-1. It plays a role in neutrophil binding to endothelial cells and subsequent extravasation to sites of inflammation.

αXβ2 (β150,95) is expressed on monocytes, granulocytes, activated B and T cells, NK cells and at high levels on macrophages. It is a marker for hairy leukemia cells.

Fibrinogen is a ligand for this integrin. Again, this integrin appears to be involved in inflammatory responses, playing a role in monocyte and granulocyte adhesion to endothelial cells although the ligand on the endothelial cells remains unidentified (see Larson and Springer review).

3. Biological and Pathological process mediated by Integrins containing the β3 subunit:

Two known parings of the β3 subunit have been observed: with αV to make αVβ3, the Vitronectin Receptor; and with GPIIb to make GPIIb-IIIa, the Fibrinogen Receptor. αVβ3 is widely distributed, is the most promiscuous member of the integrin family and mediates cellular attachment to a wide spectrum of adhesive proteins, mostly at the R-G-D sequence on the adhesive protein. The biological processes mediated by αVβ3 are diverse and include bone resorption, angiogenesis, tumor metastasis and restenosis. αVβ3 is known to signal upon adhesive protein ligation (Leavesley, P. I. et al., *J Cell Biol* (1993) 121:163–170). As an example, endothelial cells undergo apoptosis when relieved of ligation (Brooks, P. C. *Cell* (1994) 79:1157–1164).

GPIIb-IIIa, by contrast, is restricted to platelets and cells of megakaryocyted lineage although a report has appeared indicating that GPIIb-IIIa is present in tumor cell lineages. As discussed in detail elsewhere in this application, the function of GPIIb-IIIa is primarily to bind adhesive proteins to mediate platelet aggregation. In this function, GPIIb-IIIa participates in both inside-out and outside-in signaling. Decreased receptor function of GPIIb-IIIa leads to bleeding; elevated receptor function of GPIIb-IIIa can lead to thrombus formation. Studies have appeared indicating that platelet aggregation through GPIIb-IIIa may also be involved in tumor metastasis.

4. Biological and Pathological processes mediated by Integrin containing the β5 subunit:

The exact function of this integrin is not clear, however evidence exists that activation of a receptor tyrosine kinase is required in order for carcinoma cells to migrate on vitronectin using αvβ5 (Klemke, R. L. et al., *J Cell Biol* (1994) 127:859–866). Interestingly, this integrin (as well as the αvβ3 integrin) may act as receptors for adenovirus entry into cells (reviewed in Nemerow, G. R. et al, Trends in Cell Biol (1994) 4:52–55).

5. Biological and Pathological processes mediated by Integrins containing the β6 subunit:

β6 is expressed during fetal development, as well as wound healing and in epithelial tumors which suggests it may play a role in epithelial migration. Its expression can be induced in keratinocytes treated with TGF-β1, implying a role for this receptor in wound healing (Zambruno, G. et al., *J Cell Biol* (1995) 129(3):853–865). This integrin binds to fibronectin and there is evidence that the β6 cytoplasmic domain is important for some of its function. Expression of αvβ6 in a human carcinoma cell line enhances the proliferative ability of these cells in in vitro and in vivo assays, but mutant with deletions of the carboxy terminal of the β6 cytoplasmic domain no longer showed this enhanced proliferation (Agrez, M. et al., *J Cell Biol* (1994) 127:547–556).

6. Biological and Pathological processes mediated by Integrin containing the β7 subunit:

Two β7 containing integrins have been identified thus far. These are α4β7 and αEβ7 and appear to be expressed mostly on leukocytes, in particular small intestinal epithelial lymphocytes (Ni, J. et al., *Cell Immunol* (1995) 161:166–172). Their expression can also be induced on peripheral monocytes, and monocytoid cell lines, with agents such as PMA and IFNg, which promote maturation to the macrophage stage of development (Tiisala, S. et al., *Eur J Immunol* (1995) 25:411–417). These integrins play a role in intraepithelial homing. The ligands for α4β7 include fibronectin and VCAM-1 but no ligands have yet been identified for αEβ7.

F. Inhibitors of Kinases that Phosphorylate Integrins

The present invention further provides methods for reducing or blocking integrin mediated signaling which rely on blocking or reducing the level of phosphorylation of tyrosine residues found in the cytoplasmic domain of β-subunit. Since tyrosine phosphorylation in vivo is required for the association of an integrin with a signaling partner, reduction or blockage of tyrosinyl phosphorylation will result in modulating, reducing or eliminating integrin mediated signals.

In detail, integrin mediated signaling can be reduced or blocked by administering to a cell an agent which inhibits the action of tyrosine kinases. Alternatively, signaling can be reduced by supplying exogenous tyrosine phosphatase or by increasing the activity of cellular phosphatase.

As used herein, an agent is said to inhibit the action of a tyrosine kinase if the agent can reduce or eliminate the activity of a tyrosine kinase. A number of agents are presently known which can reduce the activity of tyrosine kinase, these include, but are not limited to Genistein and Herbimycin A (a bezenoid ansamycin inhibitor).

As used herein, an agent is said to increase the activity of a cellular phosphatase if the agent stimulates the production of cellular phosphatases or increases the activity of phosphatases present in a cell. Phosphatases can be activated by addition of PK-A or PK-C activators or inhibitors of serine/threonine phosphorylation (Brautigan, D. L. et al., *PNAS USA* (1991) 15:6696).

G. Administration of Agents that Affect Integrin Signaling

The agents of the present invention can be provided alone, or in combination with another agents that modulate a particular pathological process. For example, an agent of the present invention that reduces thrombosis by blocking integrin mediated cellular signaling can be administered in combination with other anti-thrombotic agents. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which block integrin/signaling partner association. While individual needs vary, determination of optimal ranges of effective amounts of each component is within the skill of the art. Typical dosages comprise 0.1 to 100 mg/kg/body wt. The preferred dosages comprise 1 to 100 mg/kg/body wt. The most preferred dosages comprise 10 to 100 mg/kg/body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals, such as humans, sheep, horses, cattle, pigs, dogs, cats, rats and mice, or in vitro.

The preferred therapeutic compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, and is a condition where there is rapid consumption of coagulation factors and systemic coagulation which results in the formation of life-threatening thrombi occurring throughout the microvasculature leading to widespread organ failure.

The compounds of this present invention, selected and used as disclosed herein, or otherwise selected and used by techniques known to the skilled artisan, are believed to be useful for preventing or treating a condition characterized by undesired thrombosis, such as in (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of -septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g., renal dialysis, cardiopulmonary bypass or other oxygenation procedure or plasmapheresis), (f) the treatment or prevention of thrombotic complications associated with instrumentation (e.g., cardiac or other intravascular catheterization, intra-aortic balloon pump, coronary stent or cardiac valve), and (g) those involved with the fitting of prosthetic devices.

Anticoagulant therapy by agents according to the present invention also are useful to prevent coagulation of stored whole blood and to prevent coagulation in other biological samples for testing or storage. Thus the compounds of this invention can be added to or contacted with any medium containing blood cells and in which it is desired that blood coagulation be inhibited, e.g., when contacting a mammal's blood with material such as vascular grafts and stents, orthopedic prostheses, cardiac stents, valves and prostheses, extracorporeal circulation systems and the like.

H. Methods for Identifying Integrin-Mediated Signaling

The present invention further provides methods for identifying cells involved in integrin-mediated signaling as well as techniques which can be applied to diagnose biological and pathological processes associated with integrin-mediated signaling.

Specifically, integrin-mediated signaling can be identified by determining whether the cytoplasmic domain of the β subunit of an integrin expressed by a particular cell is phosphorylated. Cells possessing nonphosphorylated cytoplasmic domains are not considered to be involved in integrin-mediated signaling while cells possessing phosphorylated cytoplasmic domains are. Such methods are useful in identifying sites of inflammation, thrombosis, and tumor metastasis.

In detail, an extract of cells is prepared which contains the β subunits of the cellular integrins. The cytoplasmic domains are then assayed to determine whether the tyrosine residues contained in the cytoplasmic domain are phosphorylated. The degree of phosphorylated tyrosines present in the cytoplasmic domain of the β subunits provides a measurement of the degree the cell is participating in signaling. An increase in the degree of signaling is a measurement of the level of integrin mediated activity.

For example, to determine whether a tumor has metastatic potential, an extract is made of the tumor cells and the β subunit of integrins expressed by the tumor cells are isolated using known methods such as immunoprecipitation. The cytoplasmic domain of the β subunits is then analyzed, for example, by 2-D gel electrophoresis to determine the presence or absence of phosphorylated tyrosine residues. The presence of a phosphorylated tyrosine residue correlates with the metastatic potential of the cancer.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Experimental Procedures—Platelet preparation

Blood from healthy volunteers was collected into 1/6$^{th}$ volume of 85 mM sodium citrate, 111 mM dextrose and 71 mM citric acid supplemented with 50 ng/ml PGI2 and 0.6 U/ml apyrase. After centrifugation of the blood at 160× g for 20 minutes the platelet rich plasma was removed and subjected to further centrifugation at 730× g for 10 minutes to sediment the platelets. Platelets were then resuspended in 13 mM trisodium citrate, 120 mM NaCl and 30 mM dextrose pH 7.0 and washed ×2 with this buffer. The platelets were then resuspended in 12 mM NaHCO$_3$, 138 mM NaCl, 5.5 mM dextrose, 2.9 mM KCl, 10 mM Hepes, 1 mM CaCl$_2$, 0.3 U/ml apyrase and allowed to recover for 1 hour at 37° C. Resting platelets were activated by the addition of 1 nM thrombin with stirring until aggregates were visible (1–3 minutes).

Antibodies

The anti-phosphotyrosine antibodies, 4G10 and PY-20, were obtained from UBI (Lake Placid, N.Y.) and Transduction Laboratories (Lexington, KY), respectively. The anti-tyrosine kinase antibodies used in these experiments were as follows: mouse anti-p60c-src monoclonal antibody (mAb) 327 (Oncogene Science, Uniondale, NY), rabbit anti-human p53/56lyn antisera (UBI), rabbit anti-p59fyn antisera and rabbit anti-human syk antisera (Santa Cniz Biotechnology, Santa Cruz, Calif.). The mouse anti-human GPIIIa monoclonal antibodies E8 and C3a.19.5 were raised against purified GPIIIa and a KLH-coupled cytoplasmic domain peptide of GPIIIa respectively. Rabbit anti-GRB2 antisera was from Santa Cruz Biotechnology. Rabbit anti-vav antibody was purchased from UBI. The rabbit anti-SHC antibody came from Transduction Laboratories.

In vitro kinase assays

The desired tyrosine kinase, either purified ($p_{60}^{c-src}$, Oncogene Science, or $p93^{c-fes}$, UBI) or partially purified ($p56^{lyn}$, $p59^{fyn}$, both from UBI) was incubated with the relevant substrate in 20 ml final volume kinase assay buffer (20 mM Tris-HCl pH 7.4, 10 mM MgCl$_2$, 10 mM MnCl$_2$, 0.1% NP-40 ) with 5–10 mCi of $^{32}$ P-g-ATP (Amersham, Arlington Heights, Ill.) for 10 minutes at room temperature. The substrates were present at the following concentrations: affinity purified GPIIbIIIa 2.5 mM, enolase 1.5 mM, or cytoplasmic domain peptide of GPIIIa 25 mM. Reactions were terminated by the addition of 20 ml 2× Laemmli sample buffer and boiled for 5 min. prior to loading onto gels. Bands were visualized by autoradiography using Kodak X-OMAT LS film. For some experiments the relevant tyrosine kinase was immunoprecipitated from platelet lysates using the specific anti-kinase antibody plus protein A-sepharose. The beads were then washed twice in lysis buffer, and once in kinase assay buffer prior to performing the kinase reaction. The kinase reaction was terminated by the addition of kinase wash buffer (10 mM Tris-HCl pH 7.2, 100 mM NaCl, 1 mM EDTA, 1% Triton X-100/0.3% SDS) and washed twice with this buffer.

Beads were then resuspended in 40 ml of Laemmli sample buffer, boiled for 5 min. and the supernatants loaded onto gels. Experiments looking at kinase activity associated with the GPIIIa protein were also performed as detailed above except that GPIIIa was immunoprecipitated from lysates of platelets (1% Brij 96, 150 mM NaCl, 10 mM triethanolamine, 1 mM EDTA, 1 mM sodium vanadate, 1 mM PMSF, 20 mM leupeptin, 0.15 U/ml aprotinin) and these immunoprecipitates subjected to an in vitro kinase assay which was terminated and washed in the kinase wash buffer without detergents present.

Co-immunoprecipitation experiments

Control or thrombin-aggregated platelets were lysed in the 1% Brij 96 lysis buffer. The detergent-soluble lysates were subjected to immunoprecipitation with protein A-sepharose plus an anti-tyrosine kinase antibody, the anti-GPIIIa monoclonal antibody (E8), or the relevant control antibody (either pre-immune rabbit antisera or a class-matched mouse IgG). The beads were then washed once in lysis buffer +0.5M NaCl, and twice in lysis buffer prior to boiling in Laemmli sample buffer Samples were run on 7–9% SDS polyacrylamide gels and transferred to nitrocellulose. Membranes were blocked in TBS-NP-40/4% BSA (10 mM Tris-HCl pH 8, 150 mM NaCl, 0.5% NP-40), followed by incubation with the desired antibody. Immunoreactive bands were visualized by incubating the blots for 1 h in HRP-conjugated anti-mouse or anti-rabbit IgG antibody and employing chemiluminscent detection (ECL detection kit, Amersham).

Phosphopeptide synthesis

Peptides consisting of cytoplasmic regions of GPIIIa were synthesized by SynPep corporation using solid phase Fmoc chemistry. Peptides were dissolved in 0.1% TFA/50% acetonitrile and diluted as needed.

Peptide precipitations

Biotinylated peptides (1–10 mM) were incubated with platelet lysates (either 1% NP-40 or 1% Brij 96 lysis buffer) for 90 min. at 4° C. Avidin-agarose beads were then added for a further 90 min. to precipitate the biotinylated peptides and any associated proteins. The beads were washed and then boiled in Laemmli sample buffer. The proteins were separated on SDS PAGE gels and transferred to nitrocellulose for immunoblotting with antibodies to various signaling proteins.

In vivo tyrosine phosphorylation of GPIIIa

330 μl of 3× non-reducing sample buffer containing 1 mM sodium vanadate was added to 1 ml of control or thrombin-aggregated platelets. After boiling, samples corresponding to ~1–2×10$^8$ platelets were separated in the first dimension on 7% SDS-PAGE gels. For the second dimension separation the strips were boiled in reducing sample buffer and then run on a 5% SDS-PAGE gel. These experiments were carried out in duplicate and one gel was stained with Coomassie blue to confirm total protein loading integrity while the other gel was transferred to nitrocellulose. This membrane was then immunoblotted with anti-phosphotyrosine antibodies and the relative amount of phosphorylated GPIIIa was determined by densitometry for both control and thrombin-aggregated samples. The blot was then stripped by incubation for 30 min. at 50° C. in 100 mM 2-mercaptoethanol, 2% sodium dodecyl sulfate, 62.5 mM Tris-HCl pH 6.7 and reblocked before reprobing with the anti-GPIIIa mAb C3a.19.5. Again densitometry was performed to ensure equal amounts of GPIIIa were present in both control and thrombin-aggregated samples.

Example 1

Cytoplasmic Tyrosine Phosphorylation Sites on Integrin Sub-Units

1. GPIIIa tyrosine phosphorylation in response to thrombin-stimulated aggregation GPIIb-IIIa is a member of the integrin superfamily of proteins described above. GPIIb-IIIa is used as the prototype integrin for the invention described herein.

Because of the high degree of sequence homology between integrin subunits, this invention can be applied to the family of integrins described above. Two tyrosine residues are present in the cytoplasmic domain of GPIIIa. Data presented below demonstrate that i) one of the cytoplasmic tyrosines exists in a sequence with structural features that predict that the protein should be a tyrosine kinase substrate (e.g., the structural similarity to the tyrosine phosphorylated motif found in the epidermal growth factor and insulin receptor referred to above) and ii) that the tyrosine phosphorylated cytoplasmic domain should create a motif(s) which will interact with signaling proteins.

In light of our discovery, the following observations are relevant. The NPLY SEQ ID NO: 26 sequence encompassing residues 744–747 of GPIIIa is homologous to the NPXY SEQ ID NO: 27 motif which, when phosphorylated on tyrosine, is known to bind proteins with the phosphotyrosine-binding (PTB) domain such as SHC, IRS-1, and possibly pp140 kDa (Kavanaugh, W. M. et al., *Science* (1994) 266:1862–1865; Gustafson, T. A. et al., *Mol Cell Biol* (1995) 15:2500–2508). Also there exists an immune receptor tyrosine-based activation motif (ITAM; YXXL/IXXXXXXXXYXXL/I (SEQ ID NO: 9)) found on subunits of the T cell receptor, B cell receptor, and Fc receptor which are, when phosphorylated on both tyrosines, known to interact with signaling proteins (e.g. ZAP-70 in T cells or syk in B cells) (Chan, A. C. et al., *Cell* (1992) 71:649–662; Hutchcroft, J. E. et al., *J Biol Chem* (1992) 267:8613–8619; Law, D. A. et al., *Curr Biol* (1993) 3:645–657). It is noted that the sequence in the β3 subunit, although containing two tyrosine residues, lacks the L/I residues found in all ITAM domains. Therefore, the β3 cytoplasmic domain does not appear to contain an ITAM motif. However, the cytoplasmic domain of the β4 integrin, which does not bear homology to the other integrin β subunits, does contain an ITAM domain. Like other ITAMs, this domain has recently been shown to act in the recruitment of signaling molecules (Mainiero, F. et al, *EMBO J* (1995) 14:4470–4481). Accordingly, experimental protocols were developed to determine whether the tyrosine residues within the GPIIIa were also phosphorylated in response to stimuli which activate the GPIIb-IIIa integrin.

Resting platelets were induced to aggregate by the addition of the agonist thrombin with stirring and lysates were made from both control and aggregated platelets.

When GPIIb-IIIa was immunoprecipitated from these lysates, no tyrosine phosphorylation of GPIIIa was observed in either sample when these immunoprecipitates were analyzed following SDS disc gel electrophoresis, as has been previously reported (Parise, L. V. et al., *Blood*, (1990) 75:2363–2368).

However, a three to six fold enhancement of phosphorylation of GPIIIa was observed when platelets were lysed in a high concentration of SDS and the proteins immediately separated by 2-D gel electrophoresis prior to transfer to a nitrocellulose membrane, and immunoblotting to detect phosphorylated proteins with phosphotyrosine antibodies and with a GPIIIa antibody to quantitate GPIIIa. These results show that the GPIIIa protein is phosphorylated on tyrosines, in vivo, in response to thrombin-induced aggregation (FIG. 3). Although the reason why enhanced phosphorylation of GPIIIa is not observed when lysates are immunoprecipitated with GPIIb-IIIa antibodies is not known, it is possible that the high concentration of protein phosphatases present in platelets (Frangioni, J. V. et al., *EMBO J* (1993) 12:4843–4856) precluded identification of the phosphorylated species.

Additional experiments have been performed using a 2-D gel electrophoresis protocol and have yielded further information on the tyrosine phosphorylation of GPIIIa (FIG. 3). GPIIIa tyrosine phosphorylation can be observed in platelets induced to aggregate using agonists other than thrombin. For example, treating platelets with ADP and fibrinogen allows for platelet aggregation and tyrosine phosphorylation of GPIIIa was seen. In all cases platelet aggregation appears to be a prerequisite for GPIIIa tyrosine phosphorylation. When platelets were stimulated with ADP alone, which allows for inside-out activation of GPIIb-IIIa but does not induce platelet aggregation, no increase in GPIIIa tyrosine phosphorylation was noted (See Table 1). These results indicate that the tyrosine phosphorylation of GPIIIa is most likely a consequence of outside-in GPIIb-IIIa signaling.

TABLE 1

Platelet aggregation appears to be required for GP IIIa (β3) tyrosine phosphorylation.
Platelets were stimulated with the indicated agonists. The tyrosine phosphorylation state of β3 was then determined using 2-D gel electrophoresis and anti-phosphotyrosine immunoblotting.

| Agonist | Aggregation | $\beta_3$ Phosphorylation |
| --- | --- | --- |
| Thrombin | no | no |
| Thrombin | YES | YES |
| ADP | no | no |
| ADP, fibrinogen | no | no |
| ADP, fibrinogen | YES | YES |

A number of cytoplasmic tyrosine kinases have been reported to be present in platelets and indeed several have been implicated in integrin signaling (Shattil, S. J. et al., *Curr Opin Cell Biol* (1991) 3:869–879; Clark, E. A. et al., *Science*, (1 995) 268:233–239). This includes the src-family tyrosine kinases, src and fyn, as well as the non-src-family tyrosine kinase syk. These tyrosine kinases appeared to be possible candidates for the kinase responsible for phosphorylating GPIIIa in vivo.

Figure 4A:
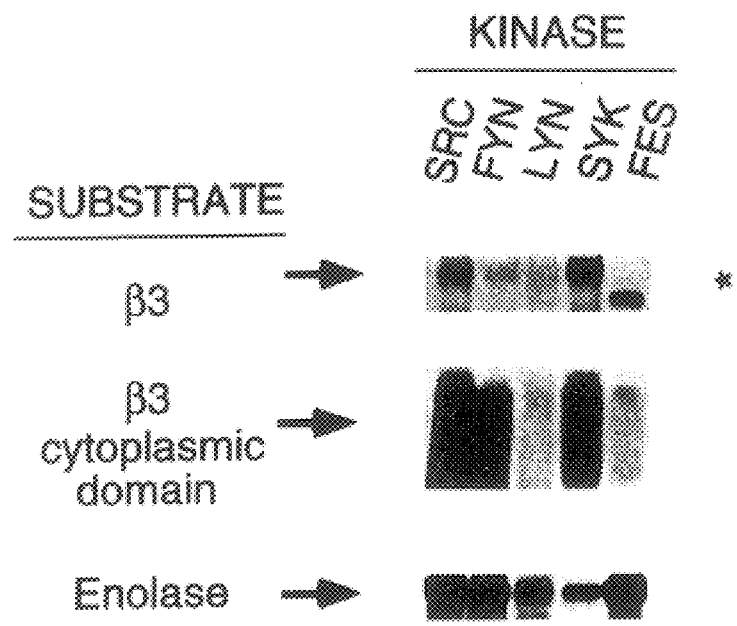

To determine which tyrosine kinases are responsible for phosphorylating GPIIIa in vivo, in vitro kinase reactions were performed to test the ability of a number of these kinases to phosphorylate both affinity-purified GPIIb-IIIa as well as a peptide consisting of the cytoplasmic domain of GPIIIa only. Purified, or partially purified, src-family tyrosine kinases p60$^{src}$, p59$^{fyn}$ and p56$^{lyn}$ were all capable of phosphorylating both the full length GPIIIa and the cytoplasmic domain peptide. The tyrosine kinase syk could also phosphorylate GPIIIa, although to a lesser degree. In contrast, the tyrosine kinase p93$^{fes}$, which contains an SH2 domain and has been implicated in signaling via certain cytokine receptors (Izuhara, K. et al., *J Biol Chem* (1994) 269:18623–18629), was unable to phosphorylate GPIIIa to any great extent (FIG. 4A). Similar results were obtained when the above-mentioned src-kinases and syk were immunoprecipitated from platelet lysates and these immunoprecipitates used in in vitro kinase assays. In these assays the src-family tyrosine kinase $p_{59}^{hck}$ was also shown to have the ability to phosphorylate GPIIIa. These data indicate that members of the src-family of tyrosine kinases, as well as the syk tyrosine kinase, phosphorylate the cytoplasmic domain of GPIIIa in vitro.

Figure 4B:
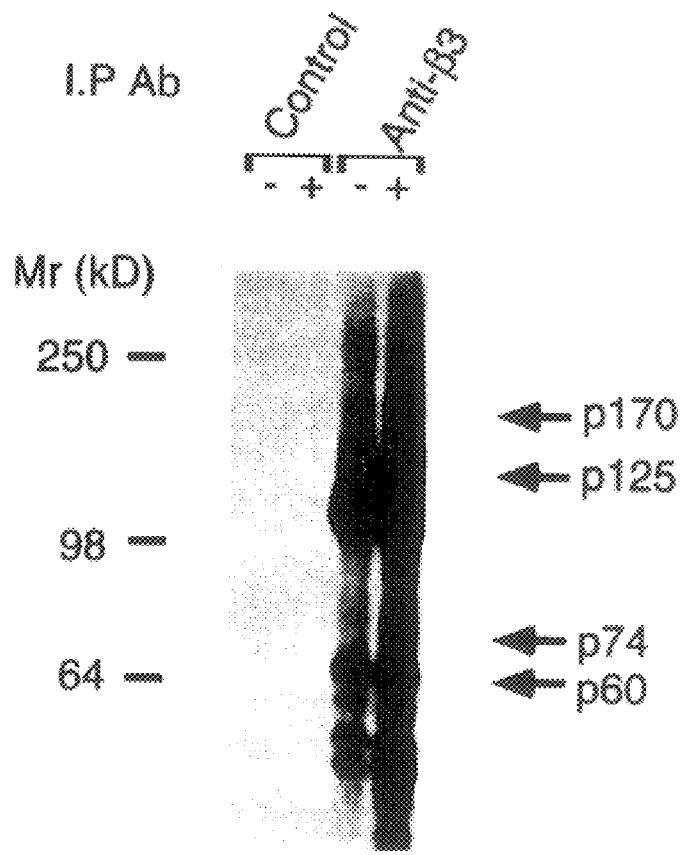

To determine which kinases are associated with GPIIIa in platelets, both control and thrombin-aggregated platelets were lysed in I % Brij-96, and GPIIb-IIIa was immunoprecipitated and the immunoprecipitate analyzed for the presence of platelet kinases. Brij-96 is a relatively mild detergent yet it appears to solubilize large complexes well (Burg, D. L. et al., *J Biol Chem* (1994) 269:28136–28142). In vitro kinase reactions were performed on the resultant immunoprecipitates to detect the kinases. An increase in the number of $^{32}P$ labeled proteins was observed in the anti-GPIIIa immunoprecipitates from the aggregated as compared to control platelet lysates (FIG. 4B). This suggested that more kinase(s) or more active kinase(s) was associating, and therefore co-immunoprecipitating, with the GPIIIa from the aggregated platelets. Interestingly, a phosphorylated protein of apparent molecular weight ~72 kD was observed in the precipitates from aggregated cell lysate. This is the same molecular weight of the syk tyrosine kinase known to have enhanced tyrosine phosphorylation in response to both inside-out and outside-in integrin signal transduction.

Various kinase re-immunoprecipitation experiments were performed in an attempt to identify the tyrosine kinases associated with GPIIb-IIIa on aggregated platelets.

First, GPIIIa was immunoprecipitated from Brij 96 platelet lysates and the immunoprecipitating material was washed under mild conditions (no detergent) in an attempt to maintain the integrity of any complexes formed between GPIIIa and cytoplasmic tyrosine kinases. The precipitated material was subjected to an in vitro kinase assay followed by re-immunoprecipitation with a variety of anti-tyrosine kinase antibodies in order to determine whether any kinases could be co-immunoprecipitated with the GPIIIa protein. To confirm these results the reverse experiment was also performed whereby various tyrosine kinases were immunoprecipitated from platelet lysates and, after an in vitro kinase reaction, were subjected to re-immunoprecipitation with an anti-GPIIIa antibody to show association of the GPIIIa with different tyrosine kinases. However, using these experimental protocols no specific tyrosine kinase could be shown to associate directly with GPIIIa, thus the responsible tyrosine kinase(s) remains unknown.

The finding that GPIIIa is tyrosine phosphorylated during platelet aggregation and identifying the kinases responsible is of fundamental importance to understanding the mechanism responsible for integrin signal transduction which allows for the integrin interaction with cytoplasmic signaling proteins. Previously, only phosphorylation of serine on GPIIIa from activated platelets has been observed. No function of serine phosphorylation is known. In contrast, the tyrosine phosphorylation of a number of cell surface receptor proteins has been shown to be critical for the signaling ability of these receptors (Weiss, A. et al., *Cell* (1994) 76:263–274).

In the case of receptor tyrosine kinases such as the PDGF receptor, ligand occupancy results in a transphosphorylation of the PDGFR cytoplasmic domains on numerous tyrosine residues. The phosphorylated tyrosines then act as binding sites for various SH2-containing proteins, for example shc, src and PLC-g, which are involved in effecting the signaling cascade. Other proteins present in cell surface immune-receptor complexes also must be phosphorylated on tyrosine residues in order for successful signaling to be initiated. Phosphorylation of the ITAM domains of these receptor complexes recruits various SH2-containing proteins, including tyrosine kinases, to the receptor complex and initiates a cascade of signaling events. Similarly, tyrosine phosphorylation of GPIIIa can be expected to allow for the interaction of GPIIb-IIIa with signaling proteins; proof that this occurs is provided below. The high degree of homology in the domains of GPIIIa which contain tyrosine to those which exist in other integrins predicts that the phosphorylation mechanism of the cytoplasmic domain of the integrin during integrin signal transduction is widely utilized within the integrin family of receptors in many different cell types.

Example 2

Interaction of Phosphorylated GPIIIa with Cytoplasmic Signaling Proteins

The discovery that the cytoplasmic domain of GPIIIa is phosphorylated at tyrosine residues during platelet aggregation was the first step in demonstrating that the phosphorylated cytoplasmic domain has functional activity in interacting with signaling proteins. A phosphorylated peptide corresponding residues 740–762 of GPIIIa was synthesized and coupled to biotin at the amino terminus:

(Peptide 1) Biotin-D-T-A-N-N-P-L-Y($PO_3$)-K-E-A-T-S-T-F-T-N-I-T-Y($PO_3$)-R-G-T-COOH (SEQ ID NO: 3)

A control peptide was synthesized with an identical sequence, but unphosphorylated:

(Peptide 2) Biotin-D-T-A-N-N-P-L-Y-K-E-A-T-S-T-F-T-N-I-T-Y-R-G-T-COOH (SEQ ID NO: 10)

Figure 5A:
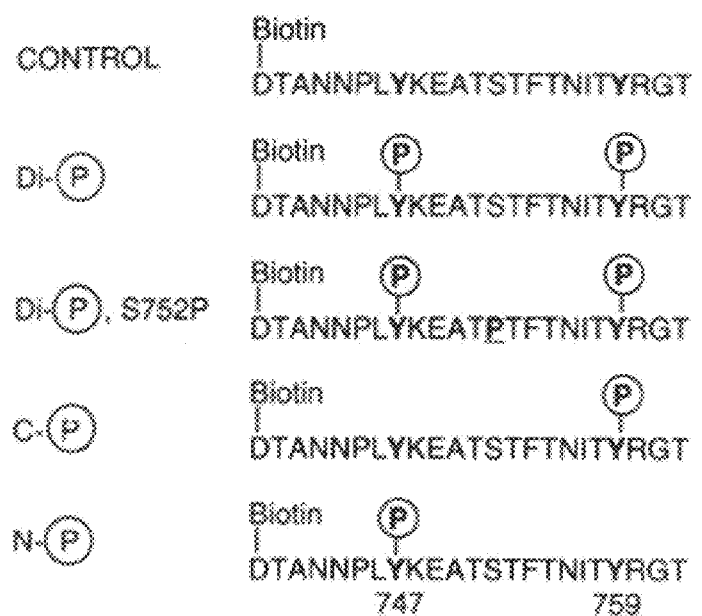
FIGS. 5A–5C show the interaction of signaling protein SHC and GR B2 with tyrosine phosphorylated β3 peptides SEQ ID NO: 23–24.
Figure 5B:
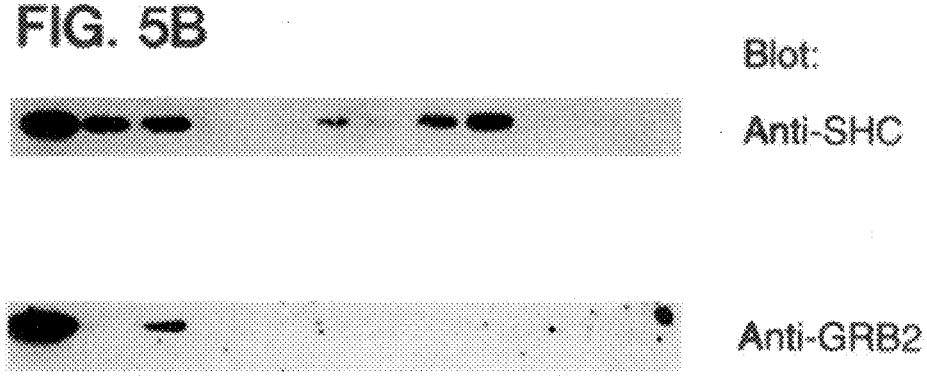
Figure 5C:
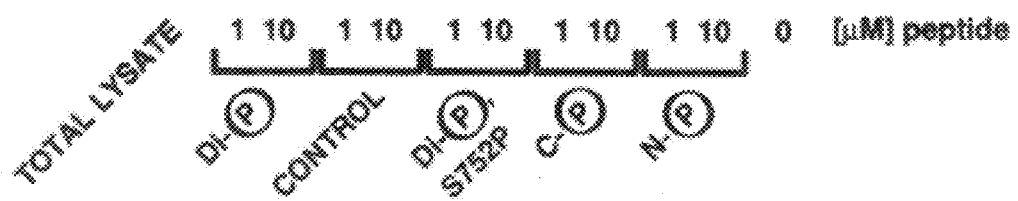

The phosphorylated peptide was tested to determine whether it had activity in interacting with signaling proteins. One method used for this purpose was adapted from a method used to examine the interaction of the phosphorylated ITAM domain from the T cell receptor with intracellular signaling proteins (Iwashima, M. et al., *Science* (1994) 263:1136–1139). Platelets were lysed with NP-40 detergent, mixed with either peptide, and the peptide with bound protein isolated by adsorption to avidin-agarose. Shc and Grb2 were two of the proteins which specifically bound to the phosphorylated peptide (Peptide 1) (FIG. 5).

The Shc signaling protein also binds to a peptide which was phosphorylated only on the carboxy-terminal tyrosine residue. To examine the physiological importance of Grb2 or Shc binding to phosphorylated GPIIIa, a doubly phosphorylated peptide which was mutated such that the serine at position 752 was changed to a proline was used. This mutation occurs naturally in a patient with Glanzmann's thrombasthenia and is known to cause signaling defects (Chen, Y. -P., et al., *Blood* (1994) 84:1857–1865). This peptide was unable to bind Grb2 and showed a markedly decreased ability to bind Shc. These results suggest that the serine to proline mutation in these patients alters protein structure such that interactions with signaling proteins cannot occur.

Another method was an adaptation of the ligand blot procedure using the phosphorylated GPIIIa cytoplasmic domain. Total platelet proteins were separated by SDS gel electrophoresis, transferred to nitrocellulose, renatured and incubated with the biotinylated peptides. Several platelet proteins were observed to bind peptide 1 but not peptide 2, the most prominent of which was a MW=230 kDa protein of unknown identity. The data show that phosphorylated GPIIIa is capable of interacting with many platelet proteins, including a signaling complex which contains Shc and Grb2, while the unphosphorylated GPIIIa is not. Since the phosphorylated peptide has this activity, the phosphorylated peptide can be used to inhibit GPIIb-IIIa signal transduction through its ability to compete for signaling proteins. A membrane permeable form of the phosphorylated peptide will therefore have utility as an antithrombotic agent to prevent platelet thrombosis.

The integrin $\alpha V\beta 3$ uses the same $\beta$ chain (GPIIIa) as does GPIIb-IIIa. As such, this integrin is phosphorylated during signal transduction. Therefore, the phosphorylated $\beta$ chain peptide will have utility in regulating the signal transduction processes of $\alpha V\beta 3$ such as angiogenesis, smooth muscle proliferation and osteoblast bone resorption, and will be useful in the treatment of cancer, restenosis and osteoporosis, respectively.

As indicated in the Background section and shown in FIG. 2, the cytoplasmic domain of GPIIIa is homologous to that of $\beta 1$, $\beta 2$, $\beta 5$, $\beta 6$ and $\beta 7$. Because the cytoplasmic domains of these $\beta$ chains all contain tyrosines at positions similar to that which is found in GPIIIa (note that $\beta 2$ only contains one), and the src family of kinases are widely distributed, these other integrins are phosphorylated in response to integrin signal transduction. Although phosphorylation has not been observed for any integrin except in vsrc transformed cells (see background), it seems probable that the same problems for detection exist as occurred with detection of GPIIIa phosphorylation in platelets. Note that mutations at the tyrosine-containing region of $\beta 1$ affected its function (see background). Phosphorylated peptides corresponding to the homologous sequences in $\beta 1$, $\beta 2$, $\beta 5$, $\beta 6$ and $\beta 7$, or mimics of these sequences, provide the structural basis for agents or targets for agents which can be used to inhibit integrin signal transductions in cells containing these $\beta$ subunits. Such agents will have utility for the treatment of, for example, cancer, restenosis and other diseases dependent upon excess cell proliferation, inflammatory diseases, Alzheimer's disease, viral infectivity, and atherosclerosis.

Example 3

Identification of Integrin Signaling Proteins

The discovery that GPIIIa is phosphorylated during platelet aggregation and specifically binds signaling proteins from platelets allows for the development of methods to discover cytoplasmic signaling proteins whose interaction with integrins is regulated by tyrosine phosphorylation. Phosphorylation on tyrosine may allow for the increased binding of proteins with either SH-2 domains or PTB domains, and proteins that bind to phosphorylated integrins should be detected because of their increased binding affinity. Phosphorylated cytoplasmic domains of the $\beta$ chains of integrin can be used as probes to probe DNA expression libraries to detect phosphorylated integrin binding proteins. Methods for such screening have been used to identify proteins that bind to other phosphorylated receptors (Margolis, B., *Proc Natl Acad Sci USA* (1992) 89:8894–8898; Skolnik, E. Y. et al., *Science* (1993) 260:1953–1955).

Alternatively, the cytoplasmic domain of GPIIIa can be used as a "bait" in a two hybrid screen in yeast, coexpressing vsrc to phosphorylate the GPIIIa moiety on the "bait". Proteins which specifically bind to the phosphorylated integrin can be identified. It is recognized that the constitutively active form of csrc may be required for this purpose. The two hybrid assay has previously been used to demonstrate the interaction of a phosphorylated protein with a signaling protein, but only on receptor kinases which autophosphorylates a tyrosine on the same expressed protein fragment.

This invention provides the method for the identification of phosphopeptide signaling proteins not associated with and autophosphorylated by a kinase. Proteins identified by these methods can be expressed and tested for their interactions with phosphorylated cytoplasmic domains of integrins. Dominant negative proteins, DNAs encoding these proteins, antibodies to these signaling proteins, peptide fragments of these proteins or mimics of these proteins may be introduced into cells and tested for their abilities to affect integrin function and/or used as pharmacological agents to affect integrin signal transduction.

Identification of the integrin signaling proteins provides the basis for a new class of therapeutics which disrupt integrin signal transduction. The newly identified proteins provide targets for screening of synthetic small molecule, combinatorial or naturally occurring compound libraries to discover agents which affect integrin signal transduction. These agent provide the basis for a new class of therapeutics which can be use to regulate integrin function.

As mentioned above, integrins comprise a family of proteins involved in many biological responses in a variety of cell types. The results with the GPIIb-IIIa integrin can be extrapolated to a number of other integrin family members as the cytoplasmic regions of the different $\beta$ subunits, in particular $\beta 1$, $\beta 5$ and $\beta 6$, show remarkable conservation of the tyrosine residues and some of the surrounding amino acids (see FIG. 2).

Example 4

$\beta 1$-Containing Integrins i. In vivo phosphorylation of $\beta 1$ integrins.

Due to the relatively large numbers of $\beta 1$-containing integrins, a number of cell types can be stimulated with the relevant ligands in order to assess the phosphorylation state of $\beta 1$ paired to a number of $\alpha$ subunits. For example, $\alpha 3\beta 1$ can be clustered using antibodies in the KB carcinoma cell line (Kornberg, L. et al., *Proc Natl Acad Sci USA* (1991) 88:8392–8396), or fibronectin can be used as a ligand for the $\alpha 4\beta 1$ and $\alpha 5\beta 1$ integrins on T cells (Yamada, A. et al., *J Immunol* (1991) 146:53–56). Based on observations with the GPIIIa molecule, where increases in tyrosine phosphorylation were not seen using traditional immunoprecipitation and 1-D gel methods, the 2-D gel technique described above is preferred for determining tyrosine phosphorylation.

ii. Ability of $\beta 1$ cytoplasmic domain phosphopeptides to bind to signaling proteins.

The following peptides are used to demonstrate the binding of signaling partners to integrins containing a phosphorylated $\beta 1$ subunit:

(peptide 1): biotin-D-T-G-E-N-P-I-Y(PO3)-K-S-A-V-T-T-V-V-N-P-K-Y(PO$_3$)-E-G-K-COOH (SEQ ID NO: 1)

and the unphosphorylated control peptide (peptide 2): biotin-D-T-G-E-N-P-I-Y-K-S-A-V-T-T-V-V-N-P-K-Y-E-G-K-COOH (SEQ ID NO: 11)

These peptides are incubated with lysates from different cells including platelets and lymphocytes (as well as other cell types in which these integrins are expressed). Then avidin-agarose is used to precipitate any proteins associating with the peptides (experimental method as detailed for GPIIb-IIIa peptides). Proteins associating with the phosphorylated peptide are signaling proteins and thus targets for therapeutics. Similarly, the peptides can be used as probes for cell lysates as well as cDNA libraries (again detailed above). The ability of the phosphopeptide to bind to signaling proteins may also allow it to function in a dominant-negative fashion.

iii. Utilizing phosphopeptides as inhibitors of signaling.

The ability of the β1 cytoplasmic domain phosphopeptide to bind signaling proteins indicates that they may act in a dominant-negative fashion when introduced into cells. The antagonistic activity peptide containing non-hydrolyzable phosphotyrosyl derivatives can be demonstrated by permeabilising cells and introducing the peptides.

The wide cellular distribution, and the number, of β1-containing integrins allows the use of a variety of cell types for which there exist well-documented methods of permeabilization. For example, T lymphocytes can be permeabilised using tetanolysin (Conti, A. et al., *J Biol Chem* (1993) 268:783–791), monocytes and other immune cells using streptolysin-O (Cunha-Melo, J. R., *J Immunol* (1989) 143:2617–2625) and platelets using a buffer containing 0.4% n-octyl-b-glucopyranoside (Hartwig, J. H. et al., *Cell*, (1995) 82:643–653). These methods of permeabilising cells result in pore formation that will readily allow for the peptides described below (approx. 3–5000 kD) to pass into the cells.

The synthesis of a suitable non-hydrolysable phosphotyrosine peptide has been described (Burke, T. R. Jr. et al., *Tetrahedron Lett* (1993) 34:4125–4128; Smyth, M. S. et al., *Tetrahedron Lett* (1994) 35:551–553; and Otaka et al., *Tetrahedron Lett* (1993) 34:7039–7042). In brief, the phosphotyrosine residues are replaced with a difluorophosphonomethyl phenylalanyl group ($F_2Pmp$) which is resistant to phosphatases. Such peptides, corresponding to the ITAM region of CD3z have been successfully introduced into permeabilised T cells and show inhibitory function (Wange, R. L. et al., *J Biol Chem* (1995) 270:944–948).

The effect of introducing the phosphopeptides into permeabilised cells is assayed in a manner suitable for the cell type used and the particular β1 integrin present on these cells. For example, the effect of the phosphopeptides on VLA-3 function in fibroblasts can be determined using binding to collagen as a readout.

By performing the experiments mentioned above, targets for therapeutics designed to inhibit signaling through the β1 integrin family can be randomly selected or rationally designed. As is obvious from the widespread distribution of these integrins, plus their involvement in a wide range of cellular activities, preventing the initial signaling event has profound effects on the cellular targets.

Example 5

β5-Containing Integrin

The β5 integrin subunit contains three tyrosine residues within its cytoplasmic domain. Residues 774 and 794 have surrounding amino acid sequences similar to those seen in the β3 subunit. Although the spacing separating the two tyrosine residues is greater (20 amino acids compared with 11 for the β3 protein) the two tyrosine residues would be on similar faces of an alpha-helix which is a possible structure of the β integrin cytoplasmic tails. This integrin can pair with the αV subunit to form a vitronectin binding receptor which is expressed on fibroblasts, carcinomas, and hepatoma cells (Diamond, M. S. et al., *Curr Biol* (1994) 4:506–517).

A similar set of experiments as those outlined above, for the β1-containing integrins, are utilized to determine the role of tyrosine phosphorylation in the function of this integrin. Particular details applying to this integrin type are provided below.

i. In vivo phosphorylation of β5 integrin.

Carcinoma cells, for example the melanoma line M21 or the FG pancreatic carcinoma line, are used in these experiments and activated by adherence to vitronectin, or possibly by clustering of the integrin using a specific antibody (β3G2, Wayner, E. A. et al., *J Cell Biol* (1991) 113:919–929). Cells are then lysed and subjected to 2-D gel electrophoresis and anti-phosphotyrosine immunoblotting as detailed previously.

ii. Ability of β5 cytoplasmic domain phosphopeptides to bind to signaling proteins.

The following peptides are used to demonstrate the binding of signaling partners to integrins containing a phosphorylated β5 subunit:

(peptide 1) biotin-E-M-A-S-N-P-L-Y($PO_3$)-R-K-P-I-S-T-H-T-V-D-F-T-F-N-K-F-N-K-S-Y($PO_3$)-N-G-T-V-D-COOH (SEQ ID NO: 4)

And the unphosphorylated control peptide:

(peptide 2) biotin-E-M-A-S-N-P-L-Y-R-K-P-I-S-T-H-T-V-D-F-T-F-N-K-F-N-K-S-Y-N-G-T-V-D-COOH (SEQ ID NO: 12)

Using the above β5 peptides it was shown that the signaling protein Shc could bind to the phosphorylated peptide (peptide 1) but not the unphosphorylated peptide 2. In these experiments the associated proteins were precipitated from lysates obtained from primary cultures of human umbilical cord venous endothelial cells (HUVECs). These cells express the vitronectin-binding αVβ5 integrin. The results with the β5 peptides indicate that extrapolating the results obtained from the β3 (GPIIIa) intergin subunit to other integrin β subunits is indeed valid.

Recent studies have established that tumor cell-induced angiogenesis can be mediated both by αVβ3, e.g., when angiogenesis is induced by basic fibroblast growth factor or tissue necrosis factor a, or αVβ5, e.g., when angiogenesis is induced by vascular endothelial cell growth factor, transforming growth factor a or by a phorbol ester (Friedlander, M. F. et al., *Science* (1995) 270:1500–1502). Since competitive antagonists of the αV integrins inhibit tumor growth, this finding indicates that inhibitors of αV-integrin signaling will be an effective anticancer drug. Both αV-containing integrins were also expressed in the actively proliferating vascular cells associated with proliferative diabetic retinopathy, while only αVβ3 was expressed in the actively proliferating vascular cells associated with age-related macular degeneration or presumed ocular histoplasmosis (Friedlander, M. F. et al., *Proc Natl Acad Sci USA* (1996) 93:9764–9769). Since competitive antagonists of ligand binding to αV-containing integrins inhibited neovascularization in experimental animals (ibid.), this finding indicates that inhibitors of αV-containing integrin signal transduction will also be effective for the treatment of diabetic retinopathy.

These peptides are used as described above for the β1 phosphopeptides, except that associated proteins are precipitated from suitable carcinoma cell lysates.

iii. β5 phosphopeptides as inhibitors of signaling.

Again, non-hydrolyzable phosphopeptides (containing $F_2Pmp$ groups as detailed above) are introduced into permeabilized carcinoma cells. The readout for effect on function for this integrin involves binding and motility on vitronectin.

Example 6

β6-Containing Integrins

Heterodimers consisting of the αV and β6 subunits have been found in certain carcinoma cell lines (Busk, M. et al.,

*J Biol Chem* (1992) 267:5790–5796), as well as epithelial cells (Breuss, J. M. et al., *J Histochem Cytochem* (1993) 41:1521–1527). β6 is expressed during fetal development, as well as wound healing and in epithelial tumors which suggests it may play a role in epithelial migration. Indeed, its expression can be induced in keratinocytes treated with TGF-β1 which implies a role for this receptor in wound healing (Zambruno, G. et al., *J Cell Biol* (1995) 129(3):853–865). This integrin binds to fibronectin and there is evidence that the β6 cytoplasmic domain is important for some of its function.

Expression of αVβ6 in a human carcinoma cell line enhances the proliferative ability of these cells in in vitro and in vivo assays, but mutants with deletions of the carboxy terminal of the β6 cytoplasmic domain no longer showed this enhanced proliferation (Agrez, M. et al., *J Cell Biol* (1994) 127:547–556).

i. In vivo phosphorylation of β6-containing integrin.

For these experiments a cell line which expresses the αVβ6 integrin (e.g. FG-2 carcinoma line) is used. The cells are activated using some form of receptor clustering, either with fibronectin or a specific antibody and then subjected to the 2-D gel and anti-phosphotyrosine immunoblotting procedure previously described.

ii. Interaction of β6 phosphopeptides with signaling proteins.

The following peptides are used to demonstrate the binding of signaling partners to integrins containing a phosphorylated β6 subunit:
(peptide 1): biotin-Q-T-G-T-N-P-L-Y(PO$_3$)-R-G-S-T-S-T-F-K-N-V-T-Y(PO$_3$)-K-H-R-E-K-Q-K-V-D-L-S-T-D-C-COOH (SEQ ID NO: 5)
The unphosphorylated control peptide:
(peptide 2): biotin-Q-T-G-T-N-P-L-Y-R-G-S-T-S-T-F-K-N-V-T-Y-K-H-R-E-K-Q-K-V-D-L-S-T-D-C-COOH (SEQ ID NO: 13)

Alternatively, a phosphorylated peptide missing the 11 carboxy terminal amino acids, which may have an influence on signaling through this integrin, can be used. This peptide is used to identify signaling proteins which do not recognize the entire cytoplasmic domain.
(peptide 3): biotin-Q-T-G-T-N-P-L-Y(PO$_3$)-R-G-S-T-S-T-F-K-N-V-T-Y(PO$_3$)-K-H-R-COOH (SEQ ID NO: 6)

iii. β6 phosphopeptides as inhibitors of signaling.

The effect of introducing non-hydrolysable derivatives (method as detailed previously) of the above peptides into permeabilised carcinoma or epithelial cell lines is assessed by cell adhesion to, and migration on, fibronectin. The β1, β5 and β6 integrin subunits described above bear the closest similarity to the β3 subunit cytoplasmic domain in that they contain at least two tyrosine residues in fairly similar positions. The β2 and β7 subunits have 1 and 2 tyrosines, respectively, in their cytoplasmic domains but in a more membrane proximal position than those of the β3 subunit. However, there is high sequence conservation in the amino acids surrounding the 5' tyrosine in both the β2 and β7 proteins and these tyrosine residues are found in the same position in each case. These residues, accordingly, are considered to be important. Similarly, the second tyrosine residue present in the β7 cytoplasmic domain is part of an NPXY SEQ ID NO: 27 motif that is found in the β1, β3, β5 and β6 subunits. This motif is also present in other signaling proteins and has been implicated as having a role in associating with signaling proteins once its tyrosine is phosphorylated (Gustafson, T. A. et al., *Mol Cell Biol* (1995) 15:2500–2508; Songyang, Z. et al., *J Biol Chem* (1995) 270:14863–14866).

Example 7

β2-Containing Integrins

The β2 subunit can pair with three different α subunits, namely αL, αM and αX. All three of these integrins are expressed mainly in cells of the immune system and have been shown to play roles in inflammatory processes. Patients who lack the β2 subunit have leukocyte adhesion deficiency, termed LAD, and these patients show an increased susceptibility to bacterial infections, chronic granulocytosis and lack of pus formation (review in Aderson, D. C. et al., *Ann Rev Med* (1 987) 38:175–194).

Experiments have suggested that the β2 subunit has signal transduction ability. For example, in a COS cell expression system, β32 was phosphorylated on serine in response to phorbol ester stimulation. Furthermore, deletion of the β2 cytoplasmic domain inhibited binding of the integrin to its ligand (Hibbs, M. L. et al., *J Exp Med* (1991) 174:1227–1238), indicating the functional importance of this region. However, based on results of mutational analysis, these authors concluded that phosphorylation of the tyrosine residue in β2 was of little or no importance in their assays. Other workers have demonstrated a role for β2 integrins in triggering tyrosine phosphorylation in neutrophils. Berton, G. et al. (J Cell Biol (1994) 126:1111–1121) have shown that clustering the β2-containing integrin on neutrophils with an anti-β2 antibody, leads to the tyrosine phosphorylation and activation of the src-family tyrosine kinase p58$^{fgr}$.

αLβ2 (LFA-1, leukoctye function associated antigen 1) is found on lymphocytes, granulocytes, monocytes and macrophages. Its expression levels are increased on memory T cells. This integrin functions in mediating the binding of leukocytes to the epithelium during inflammatory responses, a process that involves its binding to the ligand ICAM-1 (intracellular adhesion molecule 1). It is also involved in a number of the immune functions carried out by T cells, e.g. adhesion of cytotoxic T cells to their targets (reviewed in Larson, R. S. et al., *Immunol Rev* (1990) 114:181–217).

αMβ2 (Mac-1) found on monocytes, macrophages, granulocytes and NK cells. This integrin mediates adherence to both matrix and cell surface proteins. Its ligands include fibrinogen, factor X, C3bi and ICAM-1. It plays a role in neutrophil binding to endothelial cells and subsequent extravasation to sites of inflammation (see Larson and Springer review).

αXβ2 (p150,95) is expressed on monocytes, granulocytes, activated B and T cells, NK cells and at high levels on macrophages. It is a marker for hairy leukemia cells. Fibrinogen is a ligand for this integrin. Again this integrin appears to be involved in inflammatory responses, playing a role in monocyte and granulocyte adhesion to endothelial cells although the ligand on the endothelial cells remains unidentified (see Larson and Springer review). Obviously, all of the β2-containing integrins play an important role in inflammatory and immune responses.

i. In vivo phosphorylation of β2 integrins.

Using the methods described above the β2 subunit is shown to have a phosphorylated tyrosine upon integrin activation. These experiments are carried out in human blood neutrophils, or suitable macrophage or lymphocyte cell lines, depending on the particular β2 integrin studied. The integrins can be activated using immobilized anti-β2 antibody (as detailed in Berton, G. et al., *J Cell Biol* (1994) 126:1111–1121) or using a suitable ligand (e.g. fibrinogen for αXβ2).

ii. Binding of β2 cytoplasmic domain phosphopeptide to signaling molecules.

The following peptides are used to demonstrate the binding of signaling partners to integrins containing a phosphorylated β2 subunit:
(peptide 1): biotin-D-L-R-E-Y(PO₃)-R-R-F-E-K-E-K-L-S-Q-W-N-N-D-N-P-L-F-K-S-A-T-COOH (SEQ ID NO: 2)
And the unphosphorylated control peptide:
biotin-D-L-R-E-Y-R-R-F-E-K-E-K-L-S-Q-W-N-N-D-N-P-L-F-K-S-A-T-COOH (SEQ ID NO: 14)

These peptides are used to precipitate any signaling proteins, in granulocyte or lymphocyte lysates, that bound specifically to the phosphopeptide (as described above for the other β integrin subfamilies). These peptides are also used to screen leukocyte cDNA libraries to identify proteins which interact with either the non-phosphorylated and/or the phosphorylated peptide.

iii. β2 phosphopetides as inhibitors of signaling.

The non-hydrolyzable form of the above peptide 1 is introduced into permeabilised neutrophils or lymphocytes as detailed previously. Assays to test the effect of this phosphopeptide on integrin function include binding to immobilized ligand (ICAM-1 for αLβ2 and αMβ2 and fibrinogen for αXβ2) and the induction of tyrosine phosphorylation after anti-β2 antibody crosslinking.

Example 8

β7-Containing Integrins

Two β7-containing integrins have been identified thus far. These are α4β7 and αEβ7 and appear to be expressed mostly on leukocytes, in particular small intestinal epithelial lymphocytes (Ni, J. et al., *Cell Immunol* (1995) 161:166–172). Their expression can also be induced on peripheral monocytes, and monocytoid cell lines, with agents such as PMA and IFNg, which promote maturation to the macrophage stage of development (Tiisala, S. et al., *Eur J Immunol* (1995) 25:411–417). This integrin plays a role in intraepithelial homing. The ligands for α4β7 include fibronectin and VCAM-1 but no ligands have yet been identified for αEβ7. The β7 subunit contains two tyrosine residues. The membrane proximal tyrosine is conserved between the β2 and β7 subunits and the carboxy tyrosine is part of the NPXY (SEQ ID NO: 27) motif described above.

i. In vivo phosphorylation of β7 integrin.

Monocytoid lines such as THP-1 or HL-60 are cultured under conditions that induce them to differentiate into macrophage-like cells which then express the β7 integrins (Tiisala, S. et al., *Eur J Immunol* (1995) 25:411–417). The phosphorylation state of the β7 integrin is examined after stimulation by clustering the integrin with antibody or ligand (using the 2-D gel procedure already detailed).

ii. Ability of β7 phosphopetides to bind to signaling proteins.

The following peptides are used to identify signaling proteins associated with the β7 cytoplasmic tail in a phospho-dependent manner. These peptides are used to precipitate proteins from suitable cell lysates (e.g. differentiated THP-1 cells as described above), and for cDNA library screening.
biotin-D-R-R-E-Y(PO₃)-S-R-F-E-K-E-Q-Q-Q-L-N-W-K-Q-D-S-N-P-L-Y(PO₃)-K-S-A-I-COOH (SEQ ID NO: 7)
And the unphosphorylated control peptide:
biotin-D-R-R-E-Y-S-R-F-E-K-E-Q-Q-Q-L-N-W-K-Q-D-S-N-P-L-Y-K-S-A-I-COOH (SEQ ID NO: 15)

iii. Effect of β7 cytoplasmic phosphopetides on signaling.

The non-hydrolyzable derivative of the phosphopetide 1 above is introduced into permeabilised cells (of the type described above). The effect of the phosphopeptide on signaling is assessed by assays such as binding to VCAM-1 or fibronectin.

As can be seen from the above, the discovery of a mode of signaling via GPIIIa tyrosine phosphorylation and the direct binding of signaling proteins to the integrin cytoplasmic domain has far-reaching implications for the signaling and function of other integrin family members. The β subunits of the integrins show fairly high levels of sequence homology, and this is especially true with regards to the tyrosine residues in βs 3, 1, 5 and 6 and to a lesser extent with βs 7 and 2. The ability to influence signaling via these integrins using phosphopetide sequences from the relevant β-integrin cytoplasmic domains will have profound effects on a wide range of cellular activities. Potential therapeutics arising from such intervention in signaling via the β-containing integrins are discussed above.

Although the present invention has been described in detail with reference to examples above, it is understood that various modifications can be made without departing from the spirit of the invention. Accordingly, the invention is limited only by the following claims. All cited references referred to in the application are incorporated by reference.

What is claimed:

1. An assay method for identifying agents that block interactions between the cytoplasmic domain of a phosphorylated beta subunit of an integrin and a cytoplasmic signaling partner comprising the steps of:
   a) incubating a peptide comprising the phosphorylated cytoplasmic domain of the beta subunit of an integrin with a cytoplasmic signaling partner in the presence and absence of an agent, wherein said signaling partner specifically binds the phosphorylated cytoplasmic domain of said beta subunit intracellularly,
   b) detecting a change in the level of interaction between said phosphorylated cytoplasmic domain of said beta subunit and said cytoplasmic signaling partner; and
   c) determining whether said agent blocks the binding of said cytoplasmic signaling partner to said peptide in step a), wherein a decrease in the level of interaction in step b) is indicative of blocking interaction.

2. The method of claim 1 wherein said peptide comprising the phosphorylated cytoplasmic domain of the beta subunit of said integrin is selected from the group consisting of the β-1, β-2, β-3, β-5, β-6, and β-7 subunit.

3. The method of claim 1 wherein the said peptide comprising the phosphorylated cytoplasmic domain of the beta subunit of said integrin comprises an amino acid sequence selected from the group consisting of SEQ ID NO: 1, 2, 3, 4, 5, 6, 7, 10, 11, 12, 13, 14, 15 and fragments thereof capable of binding said cytoplasmic signaling partner.

4. The method of claim 1 wherein said signaling partner is contained in an extract of a cell which expresses an integrin having a phosphorylated tyrosine in the cytoplasmic domain of the beta subunit.

5. The method of claim 4 wherein said extract of a cell is prepared from a cell selected from the group consisting of platelets and leukocytes.

6. The method of claim 5 wherein said cell is activated prior to the preparation of said cell extract.

7. The method of claim 6, wherein said platelets are activated with thrombin.

* * * * *